(12) United States Patent
Brun et al.

(10) Patent No.: US 8,871,688 B2
(45) Date of Patent: Oct. 28, 2014

(54) METHOD FOR ABSOLUTE QUANTIFICATION OF POLYPEPTIDES

(75) Inventors: Virginie Brun, Seyssins (FR); Alain Dupuis, Grenoble (FR); Jerome Garin, Corenc (FR)

(73) Assignees: INSERM (Institut National de la Sante et de la Recherche Medicale), Paris (FR); Commissariat a l'Energie Atomique, Paris (FR)

( * ) Notice: Subject to any disclaimer, the term of this patent is extended or adjusted under 35 U.S.C. 154(b) by 53 days.

(21) Appl. No.: 12/602,630

(22) PCT Filed: Jun. 2, 2008

(86) PCT No.: PCT/EP2008/056795
§ 371 (c)(1),
(2), (4) Date: Dec. 1, 2009

(87) PCT Pub. No.: WO2008/145763
PCT Pub. Date: Dec. 4, 2008

(65) Prior Publication Data
US 2010/0173786 A1 Jul. 8, 2010

(30) Foreign Application Priority Data
Jun. 1, 2007 (WO) .................. PCT/IB2007/053424

(51) Int. Cl.
*C40B 70/00* (2006.01)
*G01N 33/68* (2006.01)
*C40B 30/00* (2006.01)

(52) U.S. Cl.
CPC ........ *G01N 33/6848* (2013.01); *G01N 2458/15* (2013.01)
USPC ................... 506/41; 506/30; 506/23; 506/18; 435/23; 435/4

(58) Field of Classification Search
USPC .......................... 506/41, 39, 23, 18; 435/23, 4
See application file for complete search history.

(56) References Cited

U.S. PATENT DOCUMENTS

| 7,501,286 B2 * | 3/2009 | Gygi et al. | 436/173 |
| 7,632,686 B2 * | 12/2009 | Anderson | 436/175 |
| 8,404,451 B2 * | 3/2013 | Halperin | 435/7.1 |
| 2009/0197345 A1 * | 8/2009 | Seppala | 436/89 |

FOREIGN PATENT DOCUMENTS

| WO | WO 2005116660 | * | 5/2005 |
| WO | 2006/002841 | | 1/2006 |
| WO | 2006/096704 A2 | | 9/2006 |
| WO | 2007/031080 | | 3/2007 |

OTHER PUBLICATIONS

Barker Peter E et al, "Standards for plasma and serum proteomics in early cancer detection: A Needs assessment report from the National Institute of Standards and Technology—National Cancer Institute Standards, Methods, Assays, Reagents and Technologies Worskhop, Aug. 1-19, 2005", Clinical Chemistry, vol. 52, No. 9, Sep. 2006.
Brun et al, "Isotope-labeled protein standards: Toward absolute quantitative proteomics", Molecular and cellular proteomics 2007 United States, vol. 6, No. 12, 2007, pp. 2139-2149.
Camara J. et al, "In vitro synthesis of stable isotopically labeled proteins for use as internal standards for masse spectrometric quantification of clinical protein biomarkers", National Institute of Standards and Technology, Apr. 5, 2007.
Kippen et al, "Development of an Isotope Dilution Assay for Precise Determination of Insulin, C-peptide, and Proinsulin Levels in Non-diabetic and Type II Diabetic Individuals with Comparison to Immunoassay", J Biol Chem. May 9, 1997;272(19):12513-22.
Olsen et al., "Trypsin Cleaves Exclusively C-terminal to Arginine and Lysine Residues," Mol. Cell. Proteomics, 3:608-614 (2004).
Ong et al., "Mass spectrometry-based proteomics turns quantitative," Nat. Chem. Biol., 1(5):252-262 (2005).

* cited by examiner

*Primary Examiner* — Teresa Wessendorf
(74) *Attorney, Agent, or Firm* — McAndrews, Held & Malloy Ltd.

(57) ABSTRACT

The present invention relates to a method for absolute quantification of polypeptides.

16 Claims, 12 Drawing Sheets

Figure 7

METHOD FOR ABSOLUTE QUANTIFICATION OF POLYPEPTIDES

Figure 1:
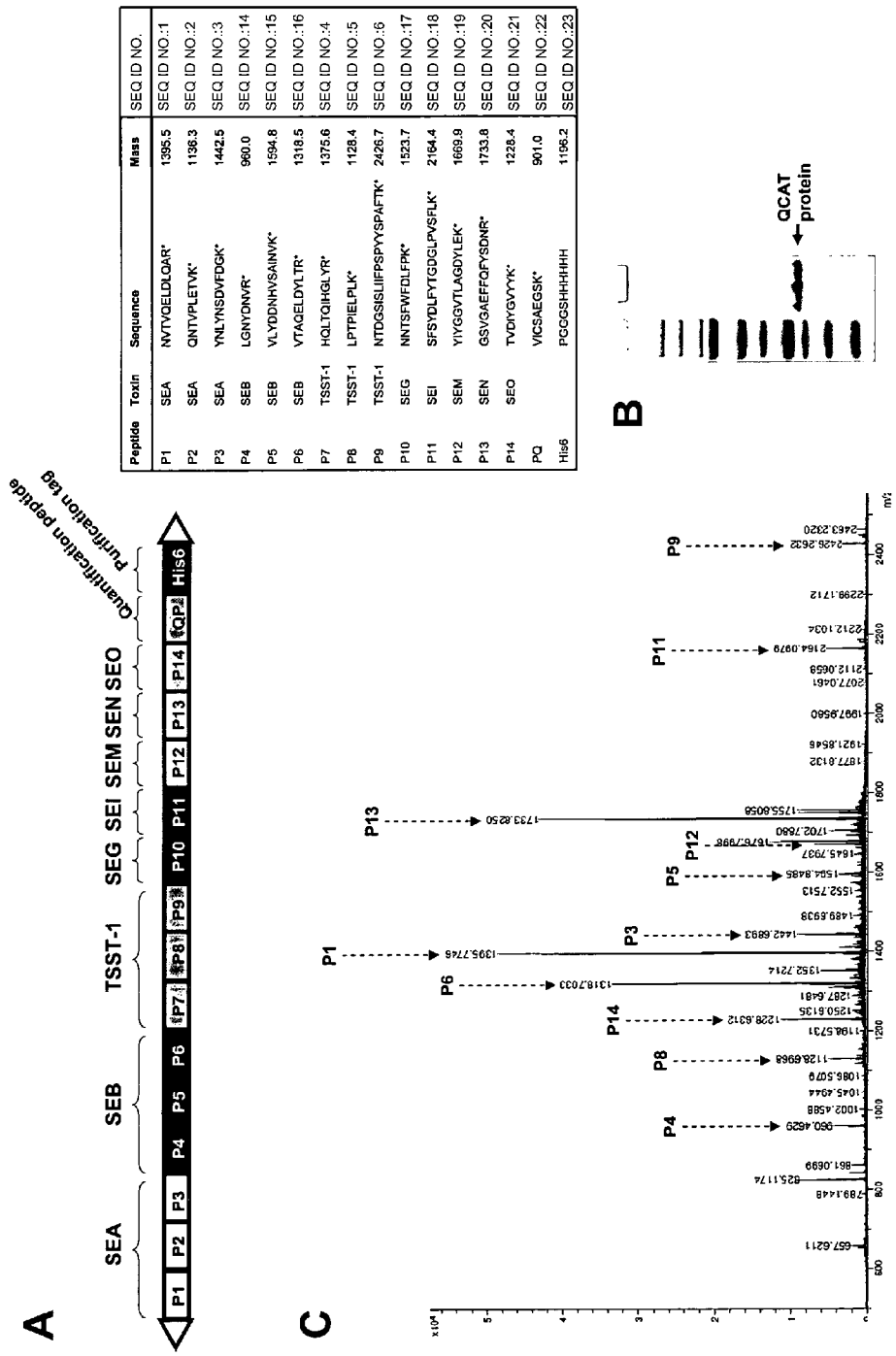

The present application is filed pursuant to 35 U.S.C. 371 as a U.S. National Phase application of International Patent Application No. PCT/EP08/56795, which was filed Jun. 2, 2008, claiming the benefit of priority to International Patent Application No. PCT/IB07/53424, which was filed on Jun. 1, 2007. The entire text of the aforementioned applications is incorporated herein by reference in its entirety.

FIELD OF THE INVENTION

The present invention relates to absolute quantification of poly peptides.

BACKGROUND OF THE INVENTION

In various fields ranging from fundamental biology to clinical diagnostic and public health surveillance, the specific and accurate quantification of proteins in complex biological samples remains a recurrent and challenging problem. For many protein biomarkers, this problem has been solved by immunological techniques. However, the success of immunological approaches relies on the heavy duty production and validation of high specificity and high affinity antibodies. Although recent efforts are being made to design antibodies arrays [20], the adaptation of immunological methods to multiplexed analyses remains limited. Indeed, the simultaneous optimization of several protein assays is hardly ever possible [21]. Alternatively, the power of MS-based proteomics can be harnessed to allow proteome-wide quantifications.

Mass spectrometry (MS) has greatly contributed to the maturation of proteomics [1]. It is now possible to characterize hundreds of proteins in an hour time frame and compare protein abundances in pairs of samples. The next frontier lies in accurate absolute quantitation. Although label-free spectral counting approaches [2, 3] are attracting considerable interest, robust absolute quantitative methodologies typically rely on the isotope dilution principle [4], in which internal standardization is achieved with isotope-labeled homologs of specific proteolytic peptides from the target protein(s) [5, 6]. The Absolute Quantitation (AQUA) peptide strategy uses chemically synthesized isotope-labeled peptides which are spiked into the samples in known quantities before MS-analysis [5-8]. The commercial availability of highly pure synthetic isotope-labeled peptides renders the AQUA peptide strategy very attractive. This methodology has been successfully used to quantify neuropeptides [23] or protein phosphorylations with phosphopeptides standards [5-7]. However, individual chemical synthesis, purification and quantification of isotope-labeled peptides make AQUA quantifications rather expensive. For this reason, proteins of interest are often quantified with a single AQUA peptide [24, 25].

Recently, the synthesis and metabolic labeling of an artificial concatemer of standard peptides (QCAT), which can be spiked into the samples before trypsin digestion, was introduced to extend the number of quantified proteins [9, 10]. QCAT and related polySIS polyproteins were developed as a smart intermediate strategy for multiplex absolute quantification of proteins. QCAT constructions allow the parallel production and quantification of several (up to 100) peptides in a single experiment. Several marker peptides representing a single protein can be included. Once conceived, a QCAT gene can easily be used for repeated production of unlimited amounts of isotope-labeled peptide standards. Interestingly, protein expression enables the synthesis of peptides difficult to produce by chemical methods such as peptides longer than 15 residues or peptides containing chemically reactive residues. According to Beynon et al [9], QCAT proteins should be especially suited for the assessment of stoichiometric ratios proteins within complexes.

The AQUA and QCAT strategies take advantage of identical chromatographic properties of an isotope labeled peptide and its unlabeled equivalent in the reverse phase chromatography step of LC-MS analyses.

Although AQUA and QCAT approaches have significantly advanced the quantitative measurement of proteins in biological samples, we discovered that the use of such standards can lead to severe biases. Calibration with AQUA peptides and QCAT constructs suffer from the following limitations: (i) a failure to take into account the actual efficiency of the proteolysis step required before MS analysis; (ii) an incompatibility with sample prefractionation which is often necessary when dealing with biological samples [11]; (iii) a poor protein sequence coverage, limiting the statistical reliability of the quantification.

Thus there is still an existing need to develop an accurate method for absolute quantification of polypeptides.

SUMMARY OF THE INVENTION

In fulfilling this object, we propose a method for quantifying a target polypeptide in a sample comprising the steps of:
(a) providing a sample to be analysed;
(b) adding a known quantity of an isotope-labeled homolog of said target polypeptide to the sample, thereby generating a spiked sample;
(c) treating the spiked sample with a protease activity to generate a plurality of proteolytic peptides;
(d) analysing the proteolytic peptides generated in step c) by mass spectrometry (MS);
(e) determining a ratio of an isotope-labeled proteolytic peptide to the corresponding unlabeled proteolytic peptide; and
(f) calculating from the ratio and the known quantity of the isotope-labeled homolog, the quantity of the target polypeptide in the sample.

The underlying principle of the method is that the isotope-labeled homolog of the target polypeptide is used as an internal standard. Provided that the concentration of the isotope-labeled homolog used as standard is itself accurately quantified, the determination of relative signal intensities during mass spectrometry analysis can be converted into absolute quantities of the target polypeptide by reference to the internal standard added in known quantity.

DETAILED DESCRIPTION OF THE INVENTION

The present invention provides a method for quantifying a target polypeptide in a sample comprising the steps of:
(a) providing a sample to be analysed;
(b) adding a known quantity of an isotope-labeled homolog of said target polypeptide to the sample, thereby generating a spiked sample;
(c) treating the spiked sample with a protease activity to generate a plurality of proteolytic peptides;
(d) analysing the proteolytic peptides generated in step c) by mass spectrometry (MS);
(e) determining a ratio of an isotope-labeled proteolytic peptide to the corresponding unlabeled proteolytic peptide; and (f) calculating from the ratio and the known quantity of the isotope-labeled homolog, the quantity of the target polypeptide in the sample.

The term "target polypeptide" refers to the polypeptide to be quantified.

The expression "isotope-labeled homolog of a polypeptide" refers to a polypeptide whose chemical structure (i.e. primary structure), except for the presence of isotope, is either identical to the non-labeled polypeptide or closely related (e.g. isoforms or variants, in particular variants with at least 90% amino-acid identity or with at least 95% amino-acid identity).

Typically the isotope-labeled homolog may be labeled with isotopes of hydrogen, nitrogen, oxygen, carbon, or sulfur. Suitable isotopes include, but are not limited to: $^2H$, $^{13}C$, $^{15}N$, $^{17}O$, $^{18}O$, or $^{34}S$. For example the homolog polypeptide may be uniformly labelled with $^{13}C$ and/or $^{15}N$. In a preferred embodiment, all amino acids of a certain type may be labeled. For example [$^{13}C$ and/or $^{15}N$]-lysine and/or [$^{15}N$ and/or $^{13}C$]-arginine residues may be used as labeling precursors when trypsin is used as the proteolytic enzyme.

Metabolic isotope incorporation may be realized by in vivo expression such as in *Escherichia coli* [9, 10, 27]. However, in vivo, the metabolism of isotope-labeled precursors (metabolic scrambling) may result in a reduced labeling yield and a dispersion of the label over different amino acids of the protein (label scrambling) [27]. In a preferred embodiment, isotope incorporation may be realized by using cell-free extracts. Due to the very limited amino-acid metabolism of cell-free extracts, in vitro isotope-labeling allows a high isotope incorporation yield (greater than 95%) with negligible scrambling [19, 28]. Another advantage of cell-free system to other in vivo labeling is the exclusive labeling of the targeted protein. Furthermore, this technique is particularly suited to toxic proteins synthesis and allows an experimental confinement that may be critical for biological and health hazard control.

As used herein, a "protease activity" is an activity which cleaves amide bonds in a polypeptide. The activity may be implemented by an enzyme such as a protease or by a chemical agent. Suitable proteases include, but are not limited to one or more of; serine proteases (e.g., such as trypsin, hepsin, SCCE, TADG12, TADG14); metalloproteases (e.g., such as PUMP-1); chymotrypsin; cathepsin; pepsin; elastase; pronase; Arg-C; Asp-N; Glu-C; Lys-C; carboxypeptidases A, B, and/or C; dispase; thermolysin; cysteine proteases such as gingipains, and the like. Proteases may be isolated from cells or obtained through recombinant techniques. Chemical agents with a protease activity such as CNBr can also be used.

"Proteolytic peptides" refers to the peptides obtained after proteolysis of a polypeptide. "Isotope-labeled proteolytic peptide" and "corresponding unlabeled proteolytic peptide" refer to a pair of peptides which have an identical chemical structure except for the presence of one or more isotope labels.

The method according to the invention may be used in a large variety of fields; such as proteomics, detection of biomarkers in biological samples, quality controls in the manufacture of vaccines and other bioproducts, biological and health hazard controls, food and water controls.

Typically the target polypeptide may be a biomarker, a protein or a fragment thereof which is physiologically or pathologically present in biological fluids (e.g. proinsulin or insulin), a bacterial protein, a viral protein, a plant protein, a yeast protein, a mold protein, a fungal protein, an animal protein or a toxin, in particular a superantigenic toxin such as a staphylococcal superantigenic toxin.

Typically the size of the target polypeptide may be larger than 5 kDa, 10 kDa, 50 kDa or 100 kDa.

Examples of samples on which the method according to the invention may be performed are biological fluids (blood, serum, plasma, cerebrospinal fluid, urine, saliva, lachrymal fluid . . . ), tissue and cells homogenates, cell culture supernantants, water, food, biocollection fluids and any biochemical fraction derived from the above materials. Biocollection fluids are fluids which are used for collecting particles which may be present in air or gas samples.

The method according to the invention may also allow the simultaneous quantification of more than one target polypeptide. In this case, known quantities of several different isotope-labeled homologs are added to the sample to be analysed. Multiplex detection and quantification of the target polypeptides may thereby be performed.

The present invention also relates to a library of isotope-labeled polypeptides. Typically a library according to the invention may contain 2, 3, 4, 5, 6, 7, 8, 9, 10, 15, 20 or more isotope-labeled polypeptides.

In a preferred embodiment of the invention, the isotope-labeled polypeptides of the library are all sensitive to the same protease, and the isotope-labeled polypeptides of the library once digested by said protease leads to singly isotope-labeled proteolytic peptides.

The present invention also relates to kit comprising as separate parts a library of isotope-labeled polypeptides and a protease.

In a preferred embodiment of the invention, the isotope-labeled polypeptide of the library once digested by the protease leads to singly isotope-labeled proteolytic peptides.

Depending of the field of application, specific libraries of isotope-labeled polypeptides may be designed. These specific libraries may, for example, facilitate the evaluation of drug efficacy and drug toxicity in humans, animals or in vitro models such as cells and tissues, the study of the pharmacokinetics features (e.g., absorption, distribution, metabolism, excretion) of therapeutic proteins, the diagnosis or prognosis of diseases in patients, the detection and identification of doping agents in athletes and horses, the detection and identification of pathogens, toxins or allergens in water, air and organic matrices such as biological fluids or food.

An embodiment of the present invention relates to a library of isotope-labeled polypeptides, wherein the isotope-labeled polypeptides of the library are biomarkers of drug efficacy or drug toxicity in humans, animals or in vitro models.

Typically said isotope-labeled poly peptides of the library may be biomarkers of hepatotoxicity, kidney toxicity, pulmonary toxicity, cardiotoxicity and/or neurological toxicity.

An embodiment of the present invention relates to a library of isotope-labeled polypeptides, wherein the isotope-labeled polypeptides of the library are therapeutic proteins.

Typically said therapeutic proteins may be selected from the group consisting of therapeutic antibodies, vaccinal antigens and immunotherapeutic allergen.

An embodiment of the present invention relates to a library of isotope-labeled polypeptides, wherein the isotope-labeled polypeptides of the library are diagnosis or prognosis biomarkers of one or more diseases.

Typically said one or more diseases may be selected from the group consisting of cardiovascular diseases, cancer diseases, metabolic diseases, neurological diseases, immunological diseases and infectious diseases.

An embodiment of the present invention relates to a library of isotope-labeled polypeptides, wherein the isotope-labeled polypeptides of the library are direct or indirect biomarkers of doping in athletes or animals such as horses.

Typically said doping biomarkers may be selected from the group consisting of erythropoietin or an analogues thereof, antiangiogenic factors, growth hormone related polypeptides, insulin analogues and insulin-like growth factors.

An embodiment of the present invention relates to a library of isotope-labeled polypeptides, wherein the isotope-labeled polypeptides of the library are biomarkers of one or more pathogens.

Typically said one or more pathogens may be selected from the group consisting of pathogenic bacteria, such as bacteria belonging to the genus *Staphylococcus, Streptococcus, Salmonella, Bordetella, Escherichia, Listeria* or *Legionella*; pathogenic viruses such as HIV or Herpesvirus; parasites such as parasites belonging to the genus *Plasmodium* or *Taxoplasma*; pathogenic fungi such as fungi belonging to the genus *Candida*; and prions.

An embodiment of the present invention relates to a library of isotope-labeled polypeptides, wherein the isotope-labeled polypeptides of the library are toxins. Typically said toxins may be selected from the group consisting of staphylococcal toxins, streptococcal toxins, shigatoxins, botulinum toxin and ricin.

An embodiment of the present invention relates to a library of isotope-labeled polypeptides, wherein the isotope-labeled polypeptides of the library are allergens. Typically said allergens may be selected from the group consisting of food allergens, plant allergens and insect sting allergens.

A further embodiment of the present invention relates to a sample collection device containing a library of isotope-labeled polypeptides according to the invention.

Typically said sample collection device may be a vial or a tube.

When a sample to be analysed is introduced into a sample collection device according to the invention, a known quantity of isotope-labeled proteins is added to the sample. This allows an early standardization of the sample and increases the accuracy of the analysis. The collection device may also contain one or more anticoagulant agents or one or more preservatives.

The collection device may also contain a matrix.

Typically the matrix may comprise the library of isotope-labeled polypeptides according to the invention. The isotope-labeled polypeptides of the library may be released from the matrix when a sample is introduced into the collection device according to the invention.

Examples of suitable matrices are gels, colloids, biphasic systems, filters or membranes. In a preferred embodiment of the invention, the matrix is a separator gel.

Typically, when the collection device containing a sample with cellular and acellular components is centrifuged, the separator gel allows the separation of cellular and acellular fractions of samples such as body fluids. Depending on their initial location within the separator gel (up or down the gel separator), the isotope-labeled polypeptides of the library are liberated either in the cellular or acellular fraction.

Targeted and untargeted mass spectrometry approaches are suited to the method according to the invention. These approaches include but are not limited to: DDA (Data Dependent Analysis), AMT (Accurate Mass and Time Tag), SRM (Single Reaction Monitoring), MRM (Multiple Reaction Monitoring) and sMRM (scheduled MRM).

A highly specific and sensitive detection as well as an accurate quantification were obtained using the MRM mode of analysis.

Concerning the mass spectrometers used, any mass analyser (time of flight, quadrupole, ion traps including linear quadrupole ion traps, ion cyclotron resonance and orbitraps . . . ) may be combined with any ionisation source (MALDI, ESI . . . ) and optionally any ion fragmentation method (in source fragmentation, collision induced dissociation, electron transfer dissociation, electron capture dissociation, infrared multiphoton dissociation, blackbody infrared radiative dissociation, surface induced dissociation . . . ).

The mass spectrometry techniques may be coupled with chromatography such as HPLC, nanoLC (1D or 2D), capillary electrophoresis.

In a further embodiment, the method comprises one or more fractionation steps between step (b) and step (d). Examples of fractionation steps are all the biochemical treatments (such as sample decomplexification, specific protein enrichment, electrophoresis or enzymatique treatment), that improves the sensitivity, precision, accuracy and reliability of quantification of the targeted poly peptide by mass spectrometry. Specific examples of fractionation steps are protein capture (chemical and immunoaffinity), immunodepletion, SDS-PAGE or 2D-PAGE, Free Flow Electrophoresis, chromatography (size exclusion, ion exchange, hydrophobicity), chromatofocusing, electrofocusing, combined fractional diagonal chromatography (COFRADIC), Equalizer technology (Biorad).

A highly specific and sensitive detection as well as an accurate quantification were obtained using immunocapture and immunodepletion.

In a preferred embodiment, the target polypeptide and its isotope-labeled homolog are either: (1) reduced and alkylated, or (2) oxidized by an oxidizing agent such as $H_2O_2$ in order to avoid any difference of oxidation state between the target polypeptide and its isotope-labeled homolog. Thus the mass spectrometry analysis is simplified. Typically the method according to the invention may comprise an additional step between step (b) and step (d), wherein the spiked sample is either reduced and alkylated or oxidized.

As the target polypeptide and its isotope-labeled homolog are submitted to the same preparation artifacts, their ratio should not be altered by preparation artifacts such as amino-acid oxidation or miscleavage. The present invention is thus adapted to the quantification of oxidation or miscleavage proned polypeptides, such as polypeptides containing methionine and/or cysteine and polypeptides presenting at their extremity a motif which is difficult to digest by a protease.

In case the target polypeptide carries post-translational modifications, such as additional functional groups, for example glycosyl or phosphoryl groups, said post-translational modifications may be removed before or just after the addition of the isotope-labeled homolog using specific enzymes such as PGNases or phosphatases. This step eliminates the heterogeneity introduced by post-translational modifications that may impair precise quantification of the target.

Alternatively, the isotope-labeled homolog nouy carry the same post translational modifications as the target polypeptide. For example, for modifications such as glycosylation, ubiquitination or phosphorylation, a strategy for phosphorylation or ubiquitination or glycosylation of the isotope-labeled homolog may be developed. In this case, the analysis allows the exclusive quantification of the post-translationally modified form of the target poly peptide.

A further embodiment of the invention relates to a method for quantifying a target polypeptide in a sample, wherein said target polypeptide carries one or more post-translational modifications, and wherein said method comprises an additional step between step (a) and step (c) of removing said one or more post-translational modifications of said target polypeptide, and wherein said isotope-labeled homolog is an isotope-labeled homolog of the polypeptide obtained by the step of removing said one or more post-translational modifications of said target polypeptide.

In case the target polypeptide is present in a sample in different forms (i.e. with one or more post-translational modifications and without), the methods of the invention with and without the step of removing the post-translational modifications of the target polypeptide may be combined to allow the quantification of the different forms of the target polypeptide.

Typically, two mass spectrometry analyses are performed. The two mass spectrometry analyses may be performed in any order.

One analysis is performed on a sample spiked with an isotope-labeled homolog of the unmodified target polypeptide without any removal of the target polypeptide's modifications. This analysis allows the exclusive quantification of the unmodified form of the target polypeptide.

Another analysis is performed on a sample in which the post-translational modifications of the target polypeptide have been removed and wherein the sample have been spiked with an isotope-labeled homolog of the polypeptide obtained by the step of removing the post-translational modifications of the target polypeptide. This analysis allows the quantification of both modified and unmodified forms of the target polypeptide.

By comparing the results of these two analyses, the relative amounts of the modified and unmodified forms of the target polypeptide can be deduced and thereby the quantity of each of the forms of the target polypeptide can be determined. Examples 4 and 5 are illustrations of this method.

In a preferred embodiment, the isotope-labeled homolog once digested by the protease used in step (c) leads to singly isotope-labeled proteolytic peptides. "Singly isotope-labeled proteolytic peptide" refers to a peptide in which a single amino-acid residue is isotope-labeled. For example [$^{13}$C and/or $^{15}$N]-lysine and [$^{15}$N and/or $^{13}$C]-arginine residues may be used as labeling precursors. This selective labeling leads after digestion by trypsin to singly labeled tryptic peptides and greatly simplifies the assignment of isotopic peptide pairs characterized by constant mass offsets.

A further embodiment of the invention relates to a kit comprising as separate parts an isotope-labeled polypeptide and a protease. This kit may be used for quantifying polypeptide with the method according to the invention. In a preferred embodiment, the isotope-labeled polypeptide once digested by the protease leads to singly isotope-labeled proteolytic peptides. For example a kit according to the invention may comprise:
  a [$^{13}$C and/or $^{15}$N]-lysine and/or [$^{15}$N and/or $^{13}$C]-arginine labeled polypeptide and trypsin.
  a [$^{13}$C and/or $^{15}$N]-lysine labeled polypeptide and endoproteinase Lys-C The kit may also comprise an antibody which recognizes the isotope-labeled polypeptide or a proteolytic peptide obtained by digestion of the isotope-labeled polypeptide by the protease.

Typically antibodies which recognize the isotope-labeled polypeptide may be used in a fractionation step such as an immunoaffinity separation step performed between step (b) and step (c) of the method according to the invention. They will recognize both target polypeptide and its isotope-labeled homolog.

Antibodies which recognize proteolytic peptide obtained by digestion of the isotope-labeled polypeptide by the protease may be used in a fractionation step such as an immunoaffinity separation step performed between step (c) and step (d) of the method according to the invention. They will recognize both isotope-labeled and non labeled proteolytic peptides.

In the following, the invention will be illustrated by means of the following examples as well as the figures.

FIGURE LEGENDS

FIG. 1. QCAT concatemer design, production and analysis 1A describes the QCAT concatemer designed to generate stable isotope-labeled peptide standards for staphylococcal superantigenic toxins. This artificial protein was constructed according to the strategy of Beynon et al [9]. The toxins targeted in the present study are SEA and TSST-1. For each of these two toxins three peptide sequences corresponding to three tryptic marker peptides were included in the QCAT concatemer (peptides P1-P3 for SEA and P7-P9 for TSST). We also added eight peptides standards for the quantification of other staphylococcal enterotoxins. These supplementary standards peptides were not used for quantification in the present study. The quantification peptide (QP) was introduced in the construct following the design of Beynon et al. However, quantification based on the unique cystein residue of this tag proved poorly reliable due to interprotein disulfide formation. Thus, we favored the more robust AAA quantification. After purification and cleavage of the purification hexahistidine-tag, the purity of in vitro produced QCAT was checked by SDS-PAGE (1B). Finally, using MALDI-TOF (1C) or nanoLC-QTOF, thirteen of the standard peptides could be assigned on a digest of the pure QCAT protein.

Figure 2:
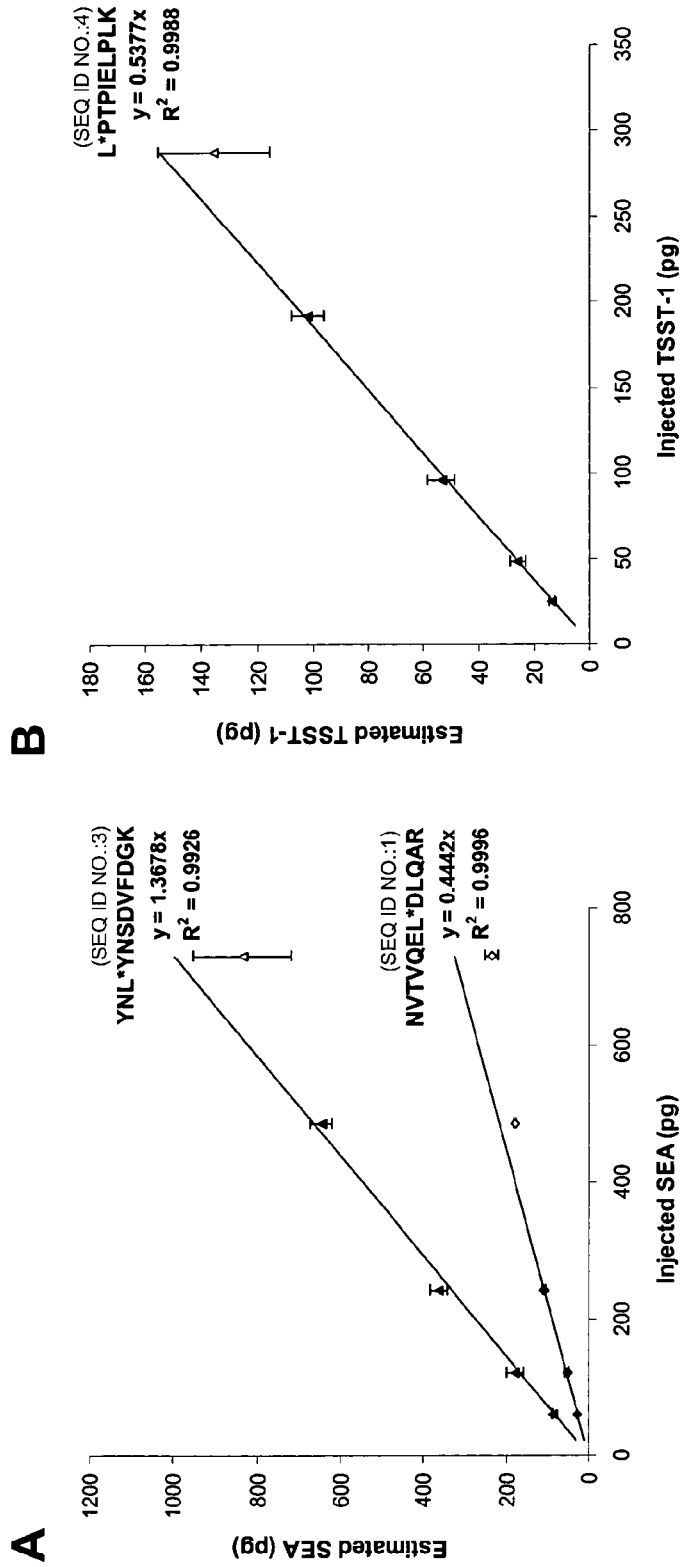

FIG. 2. Quantification of SEA and TSST-1 staphylococcal toxins in drinking water samples using AQUA peptides Variable amounts of SEA and TSST-1 were diluted in drinking water and digested in solution with trypsin. After digestion, known amounts of [$^{13}$C$_6$, $^{15}$N]-leucine (*) AQUA peptide standards were added and the samples were analyzed by nanoLC-MS. The extracted ion chromatogram signals from the unlabeled/labeled peptide doublets ($\Delta$m=7 Da) were integrated and their ratio was used to estimate the amount of natural toxin added. SEA (2A) and TSST-1 (2B) titration curves were obtained by plotting the estimate amount of toxin against the added amount. The marker peptides considered for each titration are mentioned. Each data point is the mean value±s.e.m. of 3 analytical replicates.

Figure 3:
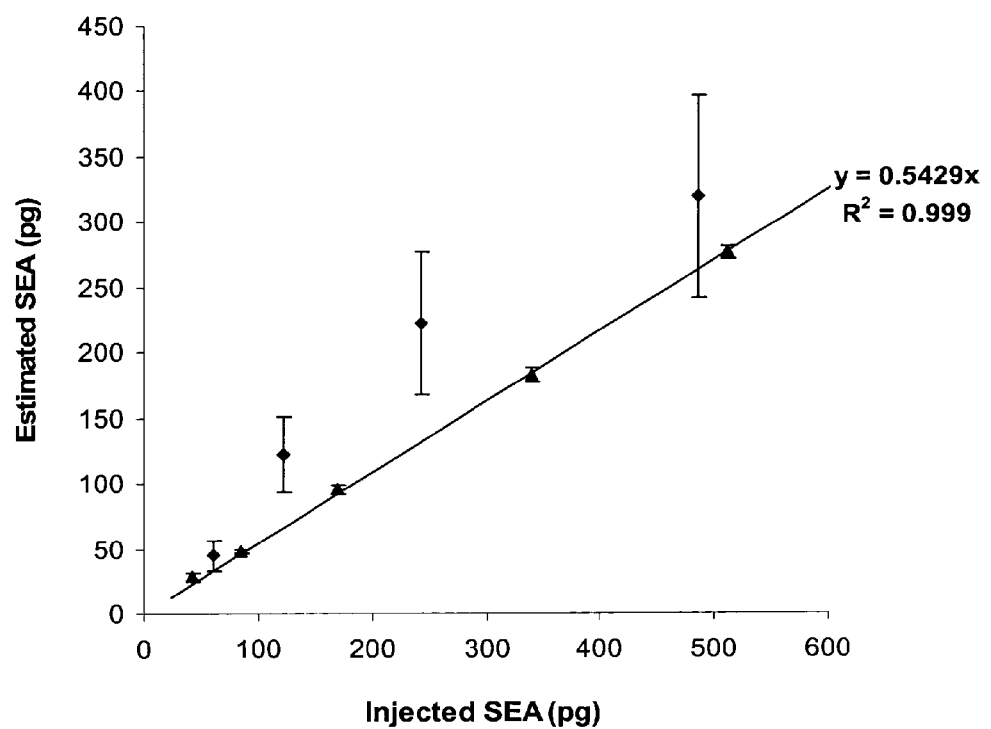

FIG. 3. Comparative use of pre-digested or co-digested QCAT standard

Variable amounts of SEA and TSST-1 were spiked into drinking water samples and QCAT concatemer was used as calibration standard. The contaminated water samples were digested in solution with trypsin either separately (♦) or concomitantly (▲) with QCAT. We show here the SEA titration curves obtained with the marker peptide YNLYNSD-VFDGK (SEQ ID NO.:3). Similar data were observed with the marker peptides NVTVQELDLQAR (SEQ ID NO.:1), QNTVPLETVK (SEQ ID NO.:2) and LPTPIELPLK. Each data point is the mean value±s.e.m. of 3 analytical replicates.

Figure 4:
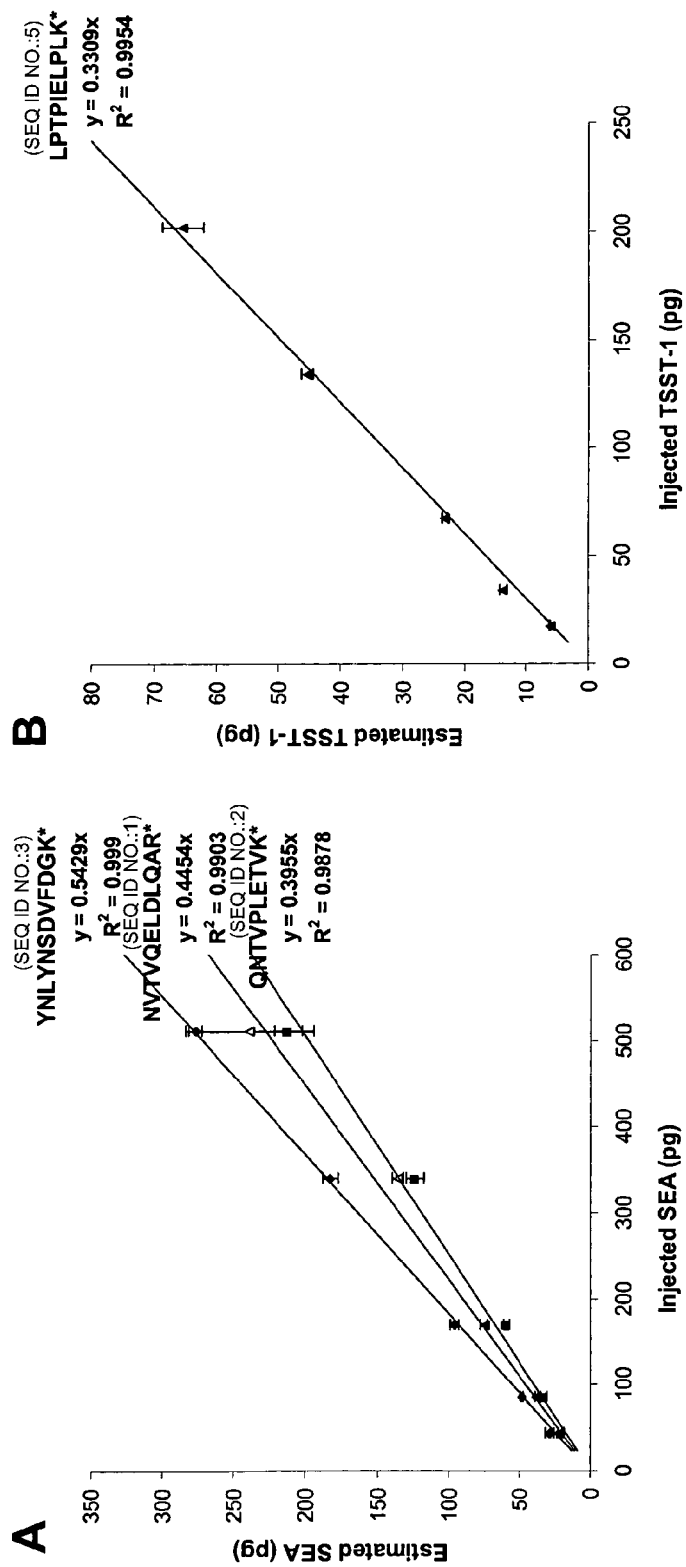

FIG. 4. Quantification of SEA and TSST-1 in drinking water samples using QCAT

Drinking water samples were contaminated with different amounts of SEA and TSST-1. QCAT concatemer was added to the samples and co-digested in solution with the toxins. The peptides generated by QCAT digestion were used as calibration standards in nanoLC-MS analysis. Three marker peptides (mentioned) enabled the titration of SEA (4A) and one peptide allowed that of TSST-1 (4B). Each data point is the mean value±s.e.m. of 3 analytical replicates.

Figure 5:
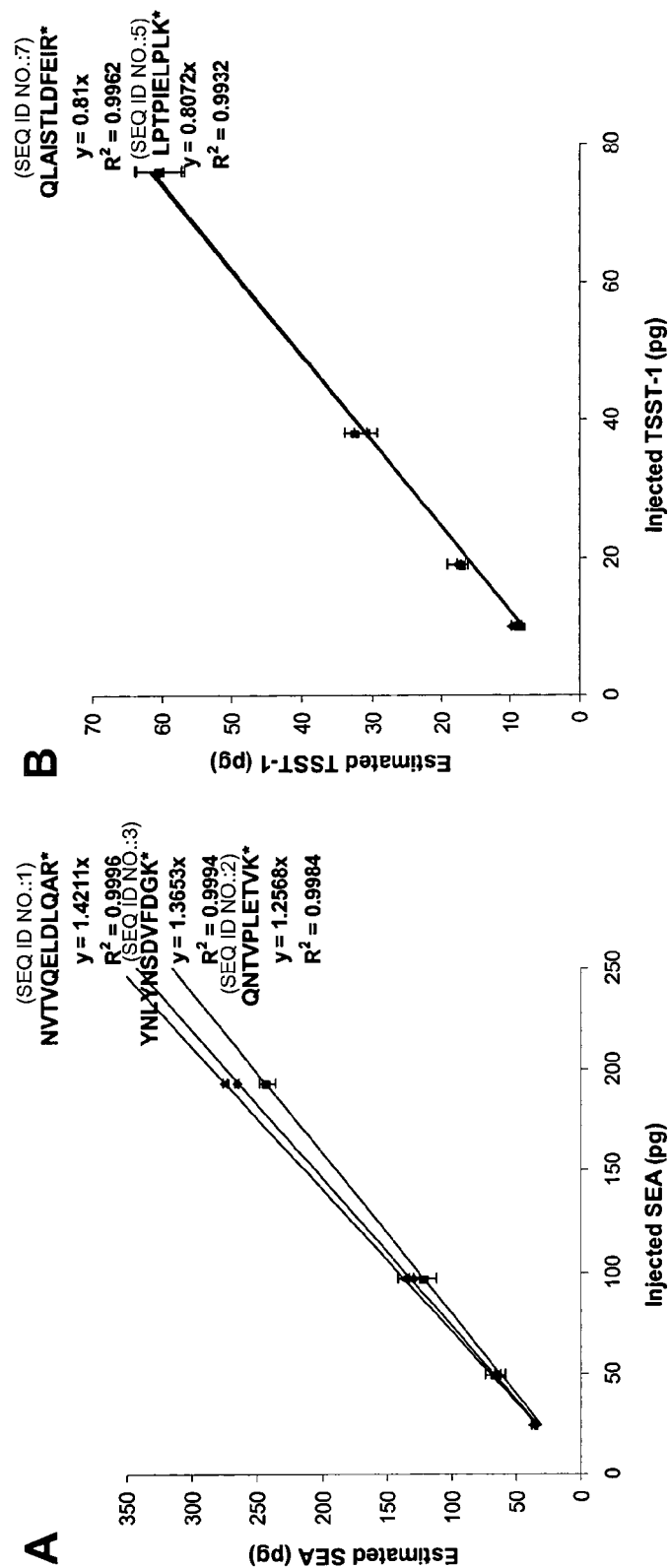

FIG. 5. Quantification of SEA and TSST-1 in drinking water samples using PSAQ standards Variable amounts of SEA and TSST-1 were spiked into drinking water samples. PSAQ full-length toxin standards were added as calibration references. The contaminated water samples were digested in solution with trypsin. The peptides generated by PSAQ toxins digestion were used as quantification references in nanoLC-MS analysis. SEA (5A) and TSST-1 (5B) were titrated with three or two marker peptides (mentioned), respectively. Each data point is the mean value±s.e.m. of 3 analytical replicates.

FIG. 6. Comparison of AQUA peptides, QCAT concatemer and PSAQ standards for the quantification of SEA and TSST-1 in urine samples peptides specifically indicated the presence of endogenous SEA and allowed quantification (typical raw data obtained with the peptide NVTVQELDLQAR (SEQ ID NO.:1) are shown).

FIG. 10. Schematic illustration of the Phospho-PSAQ method

The symbol (P) represents a phosphorylation of a serine, a threonine or a tyrosine on peptide Pep2. For the sake of clarity, in this schema, we did not represent the case of a partial phosphorylation of Peptide Pep2. This would lead to a partial depletion of the MS signal related to Pep2.

FIG. 11. Schematic illustration of the Glyco-PSAQ method

FIG. 12. Absolute quantification of staphylococcal enterotoxin A (SEA) in serum samples using PSAQ strategy.

TABLE I

Marker peptides used for the detection and quantification of SEA and TSST-1 staphylococcal superantigenic toxins.

| *Staphylococcal* superantigenic toxin | Swiss-Prot accession number | Sequence of the specific tryptic peptides used for detection and quantification analyses | Monoisotipic mass of the precursor | m/z (observed) | z (observed) | Retention time (min) |
|---|---|---|---|---|---|---|
| SEA | P0A0L2 | NVTVQELDLQAR (SEQ ID NO: 1) | 1384.7 | 693.4 | 2+ | 27.6 |
| | | QNTVPLETVK (SEQ ID NO: 2) | 1127.6 | 564.8 | 2+ | 17.7 |
| | | YNLYNSDVFDGK (SEQ ID NO: 3) | 1433.7 | 717.9 | 2+ | 32.6 |
| TSST-I | P06886 | HQLTQIHGLYR (SEQ ID NO: 4) | 1364.7 | 455.9 | 3+ | 15.8 |
| | | LPTPIELPLK (SEQ ID NO: 5) | 119.7 | 560.9 | 2+ | 36.3 |
| | | NTDGSISLIIFPSPYYSPAFTK (SEQ ID NO: 6) | 2417.2 | 806.8 | 3+ | 29.8 |
| | | QLAISTLDFEIR (SEQ ID NO: 7) | 1404.9 | 703.4 | 2+ | 43.0 |

Bolded peptides were synthesized as AQUA peptide standards

Urine samples were contaminated with different amounts of SEA and TSST-1. Three types of standards were used for toxin quantification: AQUA peptides, QCAT concatemer and PSAQ toxins. These standards were added to the samples at different stages of the analysis process (6A). The comparison of the three isotope dilution methods for the titration of SEA (peptide NVTVQELDLQAR (SEQ ID NO.:1)(6B) and TSST-1 (peptide LPTPIELPLK (SEQ ID NO.:5) (6C) is reported. Each data point is the mean value±s.e.m. of 3 analytical replicates.

FIG. 7. QCAT amino acid sequence and related DNA sequence

FIG. 8. nanoLC-NIS analysis of isotope-labeled QCAT concatemers

FIG. 9. PSAQ detection and quantification of staphylococcal enterotoxin A (SEA) in coco pearls incriminated in a staphylococcal food poisoning outbreak Coco-pearls involved in a food poisoning outbreak in France in 2006 were collected by the French Agency for Food Safety. A coco-pearl sample (25 g) was homogenized, centrifuged and the supernatant was concentrated by dialysis against polyethylene glycol. The extract was tested concomitantly using ELISA or PSAQ method. Regarding MS analysis, the concentrated extract was spiked with 100 ng of SEA PSAQ standard, immunoenriched, and submitted to SDS-PAGE and trypsin digestion. The proteolytic peptides were analyzed with nanoLC-MS analysis. Two pairs of proteotypic

TABLE II

Primers used for polymerase chain reaction analyses

| Associated Protein | Primer sequence (5' → 3') | GenBank Accession Number |
|---|---|---|
| QCAT | Forward: ggggACAAgTTTgTACAAAAAAgCAggCTATATTCAACCATgggTgCgAAAgTTA (SEQ ID NO: 8) Reverse: ggggACCACTTTgTACAAgAAAgCTgggTATgACAATATACCCgggACgACCT (SEQ ID NO: 9) | |
| SEA | Forward: TgACCCCgCggAAgCgAgAAAAgCgAAgAA (SEQ ID NO: 10) Reverse: TAAATTCCCgggTTAACTTgTATATAAATATATATCAATATgC (SEQ ID NO: 11) | M18970 |

TABLE II-continued Primers used for polymerase
chain reaction analyses

| Associated Protein | Primer sequence (5' → 3') | GenBank Accession Number |
|---|---|---|
| TSST-1 | Forward:<br>TgACCCCgCggATCTACAAACg<br>ATAATATAAggAT<br>(SEQ ID NO: 12)<br>Reverse:<br>ATTTAACCCgggTTAATTAATT<br>TCTgCTTCTATAgTTTT<br>(SEQ ID NO: 13) | J02615 |

EXAMPLES

Example 1

Summary

In this work, we present an innovative strategy (PSAQ) which uses in vitro-synthesized isotope-labeled full-length proteins as standards for absolute quantification. As those protein standards perfectly match the biochemical properties of the target proteins, they can be directly added into the samples to be analyzed, allowing a highly accurate quantification of proteins even in prefractionated complex samples. The power of our PSAQ methodology for accurate absolute quantification of biomarkers was demonstrated both on water and urine samples contaminated with *Staphylococcus aureus* superantigenic toxins as typical biomarkers of public health interest. The results obtained with the PSAQ methodology were compared with results obtained with the AQUA peptide strategy and QCAT strategy.

ABBREVIATIONS

AAA: amino acid analysis
AMT: accurate mass and time tag
AQUA: absolute quantification
DDA: data dependent analysis
ESI: electrospray
MALDI: matrix assisted laser desorption ionisation
MRM: multiple reaction monitoring
PSAQ: protein standard absolute quantification
QCAT: concatemer of standard peptides for absolute quantification
SEA: staphylococcal enterotoxin A
SEB: staphylococcal enterotoxin B
SEG: staphylococcal enterotoxin G
SEI: staphylococcal enterotoxin I
SEM: staphylococcal enterotoxin M
SEN: staphylococcal enterotoxin N
SEO: staphylococcal enterotoxin O
SRM: single reaction monitoring
sMRM: scheduled MRM
TSST-1: toxic shock syndrome toxin-1

Experimental Procedures

Chemicals and Reagents

AQUA™ [$^{13}C_6$, $^{15}N$] L-leucine-labeled peptides were synthesized by Sigma-Genosys (Saint Quentin Fallavier, France). These peptides were quantified by amino acid analysis (AAA) by the provider. Recombinant staphylococcal enterotoxins SEA and TSST-1 were purchased from Toxin Technology (Sarasota, Fla., USA). The dilutions of quantification standards and commercial toxins were systematically performed in low adsorption tubes (Dutscher, Brumath, France).

Figure 7:
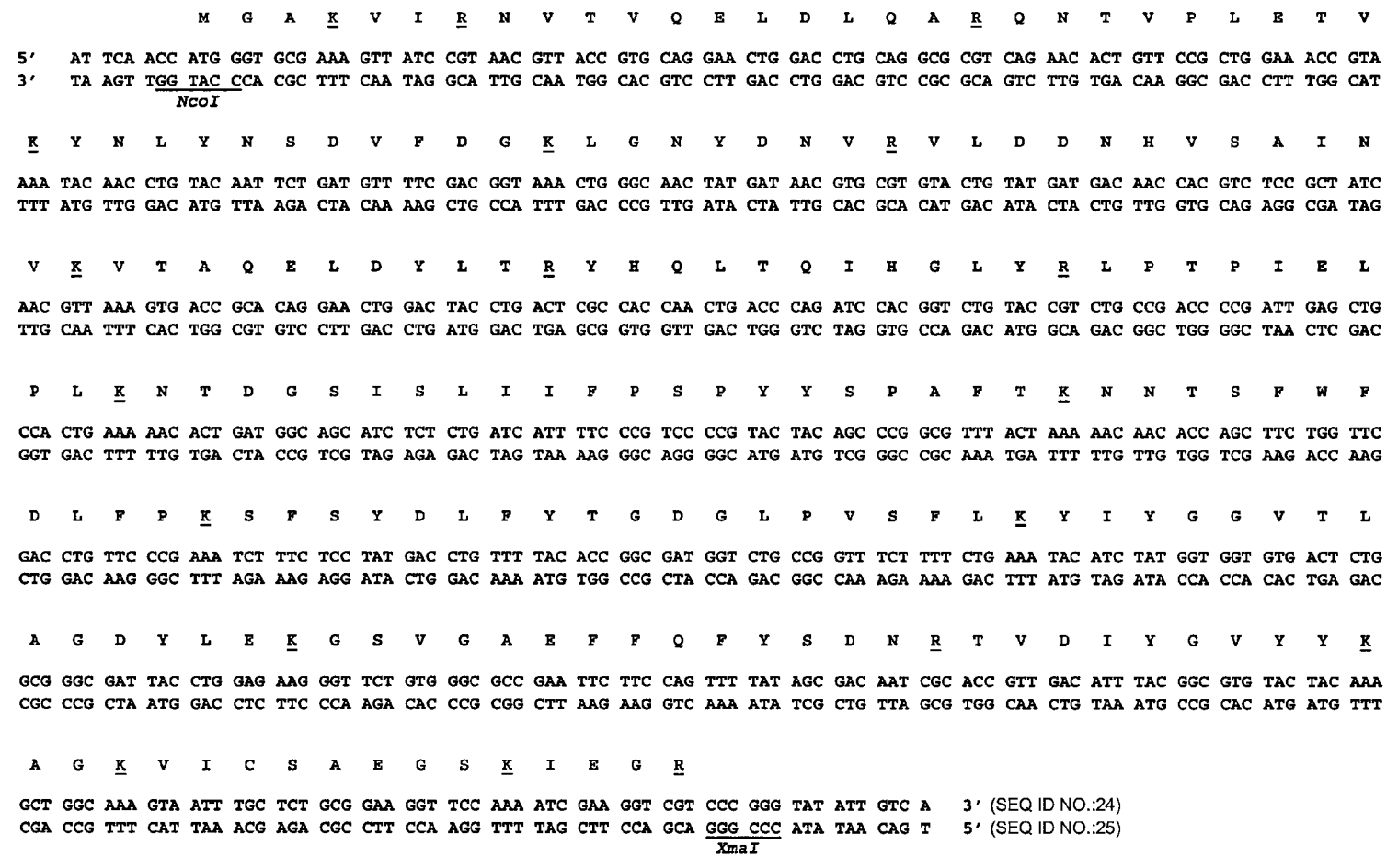
Figure 8:
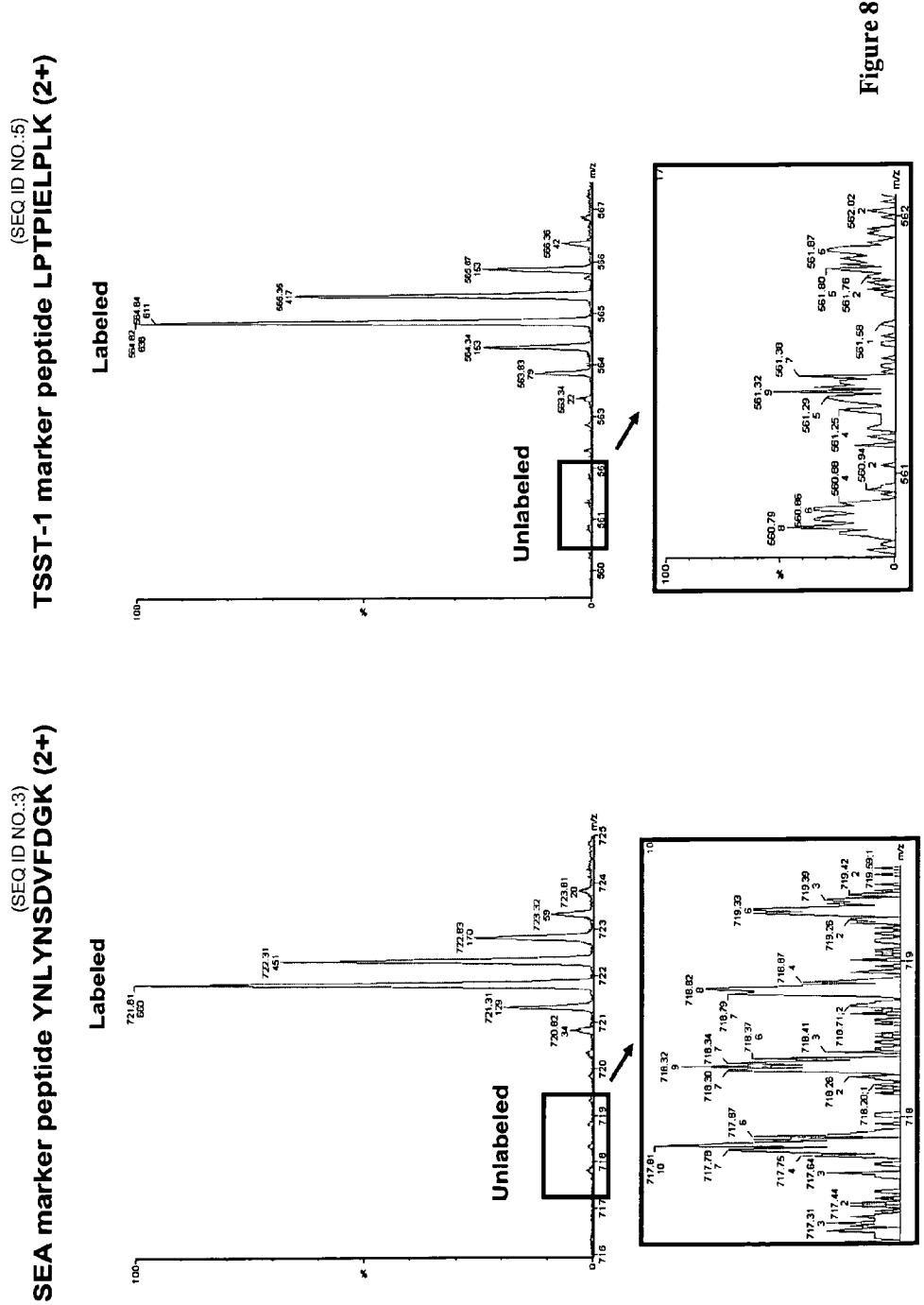

Synthesis, Purification and Quantification of the Isotope-Labeled QCAT Concatemer The QCAT protein was designed as shown in FIG. 1. Briefly, tryptic peptides from eight staphylococcal superantigenic toxins (SEA, SEB, TSST-1, SEG, SEI, SEM, SEN and SEO) were selected according to their uniqueness of sequence among the staphylococcal superantigens and their detectability in nanoLC-MS analysis. These peptide sequences were concatened into an artificial QCAT protein and retrotranslated to design the corresponding artificial QCAT gene (see reference 9 for more details). The QCAT gene was synthesized from 53 5' phosphorylated oligonucleotides (Sigma-Genosys) covering the forward and reverse strands (see FIG. 7). The synthetic QCAT gene was assembled by ligase chain reaction with Taq DNA ligase (New England Biolabs, Frankfurt, Germany) and amplified with the Expand High Fidelity polymerase (Roche, Meylan, France) using the primers mentioned in Table II. The amplified QCAT gene was purified, digested with NcoI (Roche) and SmaI (New England Biolabs) and inserted into the pIVEX 2.3d vector (Roche) providing a C-terminal hexahistidine purification tag. Ligation was achieved using the Rapid DNA Ligation Kit (Roche). The resulting plasmid was cloned into strain XL1-Blue (Stratagene, Amsterdam, Nederlands) and was purified using QIAprep Spin Miniprep Kit (Qiagen, Courtaboeuf, France). Finally, we checked the QCAT construct sequence before its use for recombinant protein synthesis (Genome Express, Meylan, France). QCAT protein production was performed in vitro using the RTS 500 ProteoMaster *E. coli* HY Kit (Roche) according to the manufacturer's instructions with the following modifications: we used the RTS Amino Acid Sampler Kit (Roche) instead of the amino-acid mix provided and we replaced L-lysine and L-arginine by isotope-labeled [$^{13}C_6$, $^{15}N_2$] L-lysine and [$^{13}C_6$, $^{15}N_4$] L-arginine (Cambridge Isotope Laboratories, Andover, Mass., USA). The isotope enrichment of [$^{13}C_6$, $^{15}N_2$] L-lysine and [$^{13}C_6$, $^{15}N_4$] L-arginine was 98% $^{13}C$ and 98% $^{15}N$. QCAT protein was efficiently produced in a precipitated form and was solubilized in guanidine 6N. QCAT purification was performed on a nickel affinity column (Ni Sepharose 6 Fax Flow, Amersham Biosciences, Freiburg, Germany) using an 20mM-250 mM imidazole gradient in guanidine 6N. After purification, QCAT was sequentially dialyzed against pure water and 1% SDS, Tris HCl 50mM, pH 7.5. QCAT quantification was performed by AAA on a Biochrom 30 Amino Acid Analyser (Biochrom, Cambridge, UK). QCAT primary structure and isotope labeling was further assessed by nanoLC-MS/MS and nanoLC-MS analysis (FIG. 8).

Synthesis, Purification and Quantification of Isotope-Labeled SEA and TSST-1 PSAQ Standards Two *Staphylococcus aureus* strains carrying SEA or TSST-1 gene were selected from the strain collection of the French National Staphylococci Reference Center. Isotope-labeled SEB standard was not synthesized as its production is officially restricted. Genomic DNA was prepared using the QIAamp DNA Stool Mini Kit (Qiagen). The primers used for PCR amplification are described in Table II. SEA and TSST-1 PCR fragments were purified, digested with KspI (Roche) and SmaI (New England Biolabs) and cloned into the pIVEX 2.4d expression vector providing a N-terminal cleavable hexahistidine purification tag (Roche). Our PSAQ strategy relies on biochemical equivalence between each toxin and its PSAQ standard. We thus privileged a N-terminus cleavable tag Co allow a polishing of the limited N-terminus heterogeneity reported for proteins produced by cell-free synthesis [16]. These constructs were cloned in XII blue, purified, sequenced and used for in vitro protein synthesis in the presence of [$^{13}C_6$, $^{15}N$] L-lysine and [$^{13}C_6$, $^{15}N$] L-arginine as described above for QCAT. Isotope-labeled SEA and TSST-1 were readily produced in a soluble form and were purified on a nickel affinity column (Ni Sepharose 6 Fast Flow, Amersham Biosciences) using an imidazole gradient. The N-terminal hexahistidine tag of each isotope-labeled protein was cleaved by biotinylated Factor Xa (Factor Xa Removal Kit, Roche) according to the manufacturer's instructions. Both the resulting hexahistidine tag peptide and the biotinylated Factor Xa were removed in a single step using a mix of streptavidin coated beads and Ni Sepharose 6 Fast Flow resin. These isotope-labeled SEA and TSST-1 were quantified by AAA. Primary structure of the proteins and labeling efficiency were verified by nanoLC-MS/MS and nanoLC-MS analysis [data not shown].

SDS-PAGE Quality Control

The home produced recombinant PSAQ proteins as well as the purchased SEA and TSST-1 were all checked for purity on SDS-PAGE using both Imperial Protein Stain and SYPRO Ruby staining (Biorad, Marnes-la-Coquette, France). The quantities of commercial toxins were too limited for AAA analysis and commercial TSST-1 toxin displayed a significant contamination precluding an accurate AAA quantification. Thus, commercial toxins were systematically quantified by comparison with our AAA calibrated PSAQ standards on SDS-PAGE using SYPRO Ruby staining [17]. SYPRO Ruby fluorescence was scanned (Laser 532 nm, filter 610BP30) on a Typhoon 9400 (Amersham Biosciences).

Water Samples Preparation and Trypsin Digestion for Mass Spectrometry Analyses

Drinking water samples were contaminated with five different quantities of SEA and TSST-1 commercial toxins. Each sample was divided into nine aliquots of 120 µl each. Three aliquots (analytical replicates) of each sample were spiked with either QCAT or PSAQ toxins standards in defined quantities. Trypsin digestion was performed in solution using sequencing grade modified trypsin (Promega, Madison, Wis., USA) at a 1:2 protease to toxins ratio in 25 mM $NH_4HCO_3$ overnight at 37° C. Samples were dried by vacuum centrifugation and resolubilized in 5% ACN, 0.2% formic acid. Before nanoLC-MS analysis, AQUA peptides were added in defined quantities into the aliquots that contained neither QCAT nor PSAQ standards.

Urine Samples Preparation and Trypsin Digestion for Mass Spectrometry Analyses

Urine from a thirty year-old healthy woman was collected and contaminated with four different quantities of SEA and TSST-1 commercial toxins. Each sample was divided into nine aliquots of 100 µl each. Three aliquots (analytical replicates) of each sample were contaminated with PSAQ toxin standards in defined amounts (FIG. 6A). Each 100 µl aliquot was adsorbed on 5 µl of Strataclean resin (Stratagene) according to the manufacturer's instructions. Following elimination of supernatant, proteins adsorbed onto the resin were directly eluted in 10 µl of a depolymerization buffer containing 2% SDS and 5% β-mercaptoethanol. At this stage, QCAT standard was added in controlled quantities into half of the samples devoid of PSAQ standards (FIG. 6A). After a thermal denaturation step at 95° C. for 5 min samples were loaded on a precast Novex NuPAGE Bis-Tris gels (4-12% acrylamide gradient) purchased from Invitrogen (Cergy Pontoise, France). Gels were run for 30 min under 200V, fixed for 30 min in 30% ethanol-7.5% acetic acid and stained with Biosafe Coomassie blue (Biorad). In the 25 kDa region of the gel encompassing toxins and QCAT, protein bands were excised and were destained by repeated cycles of incubation in 25 mM $NH_4HCO_3$ for 15 min and then with 50% (v/v) ACN in the same buffer (25 mM $NH_4HCO_3$) for 15 min. After drying by vacuum centrifugation, the gel pieces were incubated with an oxidizing solution (7% $H_2O_2$) for 15 min [18]. Gel pieces were then washed in HPLC grade water (Sigma-Aldrich) for 15 min before being dehydrated with 100% ACN. In-gel digestion was performed using 1:2 trypsin to protein ratio (sequencing grade modified trypsin, Promega) in 25 mM $NH_4HCO_3$ overnight at 37° C. Peptides were extracted from the gel using passive diffusion in the following solutions: 50% ACN, then 5% formic acid, and finally 100% ACN. The extracts were dried by vacuum centrifugation and peptides were resolubilized in 5% ACN, 0.2% formic acid. Before nanoLC-MS analysis, controlled amounts of AQUA peptides were added to the samples that had not been spiked with PSAQ or QCAT standards (FIG. 6A).

NanoLC-MS and NanoLC-MS/MS Analyses

Mass spectrometry analyses were performed on a nanoLC system coupled to a QTOF Ultima mass spectrometer (Waters, Milford, Mass., USA). Briefly, peptide digests were first concentrated on a 300 µm×5 mm PepMap C18 precolumn (LC-Packings-Dionex, Sunnyvale, Calif., USA). Peptide digests were then passed onto a C18 column (75 µm×150 mm) (LC-Packings-Dionex) and eluted with a gradient from 10% ACN, 0.1% formic acid to 80% ACN, 0.08% formic acid (run duration 60 min, flow rate 200 nl/min). The mass spectrometer was operated in the positive ion electrospray ionization mode with a resolution of 9,000-11,000 full-width half-maximum. Data-dependent analysis was employed for MS/MS (three most abundant ions in each cycle): 1 s mass spectrometry (m/z 400-1,600) and maximum 4 s NIS/MS (m/z 50-2,000, continuum mode) with 2 min dynamic exclusion. MS/MS raw data were processed using MassLynx 4.0 software (smooth 3/2 Savitzky Golay) (Waters). Peptide identifications from the resulting MS/MS dataset were achieved using an in-house MASCOT server (version 2.0) (Matrix Sciences, London, UK). Quantification was done manually from nano-LC-MS data after integration of peaks for unlabeled/labeled peptide pairs on reconstituted chromatograms obtained by extraction of a specific mass (±0.1 Da) with MassLynx 4.0 software. The minimum signal to noise ratio considered for quantitation was 15:1.

Results

Evaluation of the Commercial Toxins Solutions

SEA and TSST-1 amounts commercially supplied were re-evaluated in comparison with our isotope-labeled toxin standards preliminarily quantified by AAA. A SDS-PAGE analysis revealed that commercial TSST-1 was slightly contaminated by a higher molecular weight protein and that the commercial SEA toxin was as pure as our SEA PSAQ standard. However, when checked on two different batches, the announced concentrations of commercial SEA and TSST toxins were consistently overestimated in comparison to our AAA calibrated PSAQ standards. Accordingly, the amounts of these commercial toxins were systematically re-evaluated on SDS-PAGE using SYPRO Ruby staining [17].

Selection of Staphylococcal Superantigenic Toxins Marker Peptides

SEA and TSST-1 recombinant staphylococcal toxins were submitted to SDS-PAGE and in-gel digestion with trypsin. The peptide digests were analyzed by nanoLC-MS/MS and nanoLC-MS. Specific tryptic peptides (marker peptides) were selected for each of the two toxins (Table I). Marker peptides were chosen according to their sequence uniqueness among staphylococcal superantigens and their optimal detectability in MS analysis. Three of these marker peptides (bolded in Table I) were made synthesized as AQUA peptides with one [$^{13}C_6$, $^{15}N$] L-leucine (mass increase 7 Da).

Quantification of Staphylococcal Superantigenic Toxins in Drinking Water Using Isotope-labeled AQUA Peptides Commercial SEA and TSST-1 staphylococcal toxins were added in defined amounts into drinking water. Trypsin digestion was performed in-solution. Known amounts of AQUA peptides were added to the peptide digests before nanoLC-MS analysis. For the three unlabeled/labeled peptide pairs selected (see Table I), peak doublets separated by a mass of $\Delta m$=7 Da ([$^{13}C_6$, $^{15}N$] L-leucine peptides) were observed in the MS survey. Each of these peak doublets was integrated to determine the total ion signal of the natural peptide (mass m) and its corresponding labeled AQUA standard (mass m+$\Delta$m). The ratio of these signals allowed a direct calculation of the estimated natural toxin amount which was plotted against the added amount (FIG. 2).

Ideally, 100% recovery should have been observed. The SEA and TSST-1 titration curves obtained were linear for added amounts of toxins ranging from 50 to 750 pg. Deviation from linearity above these values resulted from ion signal saturation. The measurements of accuracy and precision were evaluated through the slope values of the titration curves and the standard mean errors (s.e.m.) values of the data, respectively. AQUA peptide standardization is a highly precise quantification strategy (FIG. 2). However, regarding accuracy, an important discrepancy between the two AQUA peptides targeting SEA was observed (slope value=1.37 for YNLYNSDVFDGK (SEQ ID NO.:3)peptide and slope value=0.44 for NVTVQELDQAR (SEQ ID NO.:1) peptide) (FIG. 2A). Three potential biases may account for such results: i) AQUA peptides were quantified by the provider using AAA, obtained lyophilized, and re-solubilized according to the provider's own guidelines. Nevertheless, quantitative re-solubilization should not be taken for granted, and a subsequent evaluation of the re-solubilized peptide by AAA would require much more material than provided, ii) AQUA standards have to be highly diluted prior to their addition into the samples. Depending on their physico-chemical properties, dilution of pure peptides can lead to important losses of peptide by adsorption onto vials, iii) Standardization with AQUA peptides does not take into account the yield of the protease digestion step. This step introduces variability from protein to protein due to the intrinsic susceptibility of each protein to proteolysis. In addition, variability between samples can also originate from the digestion conditions (composition of the sample buffer, amount of trypsin, temperature during incubation . . . ). Standard peptide adsorption onto vials or incomplete solubilization both lead to an overestimation of the true standard concentration and consequently of the targeted protein. Accordingly, the 37% overestimation of SEA abundance given by the AQUA peptide YNLYNSDVFDGK (SEQ ID NO.:1)(slope value=1.37) likely resulted from incomplete re-solubilization and/or partial adsorption of this standard peptide onto vials. Conversely, the peptides NVTVQELDQAR (SEQ ID NO.:1)and LPTPIELPLK (SEQ ID NO.:5) may not have been efficiently generated by trypsin digestion and therefore led to an important underestimation of SEA and TSST-1 abundances (slope values=0.44 and 0.54, respectively). This stresses a major limitation of the AQUA peptide strategy: it does not take into account the actual digestion yield of the different peptides from the native protein. Actually, this drawback is especially problematic for proteins such as staphylococcal superantigenic toxins which are known to be resistant to proteolysis [13].

Quantification of Staphylococcal Superantigenic Toxins in Drinking Water Using Isotope-labeled QCAT Protein We designed and produced an isotope-labeled concatemer of staphylococcal superantigenic toxins marker peptides (QCAT) (FIGS. 1A and 1B). In this construction, we included all the peptides previously chosen as AQUA standards. The presence of multiple peptide standards for each toxin aimed at improving the quantification robustness. When QCAT was digested and analyzed, among the 14 marker peptides theorically generated, 11 were detected by MALDI-TOF analysis (FIG. 1C) and 13 were observed in nanoLC-MS analysis [data not shown]. The remaining peptide (peptide P11, FIG. 1A) was not observed in nanoLC-MS analyses possibly due to its high hydrophobicity.

In agreement with previous reports [19], the cell-free expression of QCAT in the presence of [$^{13}C_6$, $^{15}N_2$]-lysine and [$^{13}C_6$, $^{15}N_4$]-arginine yielded a high rate of isotope-label incorporation. A nanoLC-MS analysis of the pure isotope-labeled QCAT indicated an isotopic purity greater than 98% (FIG. 8). Moreover, [$^{13}C_6$, $^{15}N_2$]-lysine and [$^{13}C_6$, $^{15}N_4$]-arginine-labeling leads to constant mass increments of arginyl and lysyl peptides after trypsin cleavage which greatly simplifies the processing of LC-MS data required for quantification. Therefore, for each of the marker peptides selected (Table I) peak doublets separated by a mass of 8 Da ([$^{13}C_6$, $^{15}N_2$]-lysine-labeled peptides) or 10 Da [$^{13}C_6$, $^{15}N_4$]-arginine-labeled peptides) were investigated. The ratios of unlabeled over labeled peptide signals allowed a direct calculation of the estimated natural toxin amount which was plotted against the added amount (FIGS. 3 and 4).

We showed from the previous AQUA titrations that the tryptic digestion efficiency influenced the quantification accuracy. The intrinsic susceptibility of proteins to proteolysis and the experimental conditions of the digestion may constitute major influencing parameters. In an attempt to underline the role of proteolysis conditions, two experiments were designed with the QCAT chimeric protein. In the first experiment, QCAT was digested separately and the resulting digest was used as a mixture of standard peptides to calibrate the toxins digests. In the second experiment, QCAT was added in known amounts into drinking water samples and was co-digested with the toxins. As shown in FIG. 3, poor linearity and high s.e.m. were obtained when the QCAT standard was digested separately. These results emphasize the benefits of co-digesting the standard with the target proteins for linear and reproductible quantitations.

Therefore, in subsequent experiments aimed at quantifying SEA and TSST-1 in drinking water, the QCAT standard was co-digested with the artificially contaminated samples. Although, the six marker peptides could be observed in nanoLC-MS analysis, they exhibited quite different MS detectability. In order to enhance quantification sensitivity, we focused on the four marker peptides that gave the best nanoLC-MS signals (ion signal intensity, nanoLC-peak shape) (NVTVQELDLQAR (SEQ ID NO.:1), QNTVPLETVK (SEQ ID NO.:2), YNLYNSDVFDGK (SEQ ID NO.:3) for SEA and LPTPIELPLK (SEQ ID NO.: 5) for TSST-1). In contrast with SEA titrations obtained with the two AQUA peptides YNLYNSDVFDGK (SEQ ID NO.:3) and NVTVQELDLQAR (SEQ ID NO.:1), the three QCAT-generated SEA peptide standards displayed only limited variance (compare FIG. 2A and FIG. 4A). This higher consistency is attributed to the equistoichiometric representation of peptide standards in the QCAT construct. However, QCAT quantifications led to an underestimation of SEA and TSST-1 by a factor over two-fold (FIGS. 4A and 4B). As staphylococcal enterotoxins are reputed as poorly protease sensitive [13] and QCAT concatemers are reported to be highly susceptible to trypsin digestion [9], the straightforward rational for this underestimation is to postulate different digestion rates between the toxins and the QCAT protein.

Quantification of Staphylococcal Superantigenic Toxins in Drinking Water Using Isotope-labeled PSAQ Standards Commercial SEA and TSST-1 toxins were added in defined amounts into drinking water samples. These samples were spiked with known quantities of SEA and TSST-1 PSAQ standards. The incorporation yield of [$^{13}C_6$, $^{15}N_2$]-lysine and [$^{13}C_6$, $^{15}N_4$]-arginine in these cell-free expressed standards was greater than 98% [data not shown].

The water samples were digested in solution and nanoLC-MS data were analyzed as described for QCAT. As shown in FIG. 5, SEA and TSST-1 PSAQ standards allowed quantification with three and two unlabeled/labeled marker peptides pairs, respectively. This represented an increase in sequence coverage for TSST-1. Calibration with PSAQ standards was highly precise and improved the accuracy of measurements. Regarding SEA, the results obtained using the three standard peptides were highly consistent but slightly overestimated (slope values ranging from 1.26 to 1.42). This likely originated from the partial adsorption of SEA PSAQ standard onto vials during the dilution process. In the case of TSST-1, the two standard peptides LPTPIELPLK (SEQ ID NO.:5) and QLAISTLDFEIR (SEQ ID NO.:7) both allowed a recovery of 81% (slope value=0.81).

Quantification of Staphylococcal Superantigenie Toxins in Prefractionated Urine

In the final set of experiments, we contaminated human urine samples with SEA and TSST-1 which are the most frequently involved toxins in staphylococcal toxic shock syndrome [13, 14]. Contaminated samples were prefractionated on Strataclean resin, decomplexified by SDS-PAGE and digested in-gel with trypsin. These samples were spiked with either PSAQ toxins, or QCAT concatemer, or AQUA peptides (FIG. 6A). The PSAQ standards were directly added in known quantities into the urine samples. Regarding QCAT standard, we improved the previously described QCAT concept [9] by adjusting its molecular weight to that of the target toxins (24 kDa), so that: (i) it co-migrates with the toxin targets in an electrophoresis gel, (ii) it is co-digested in-gel with the toxins and (iii) the peptides generated by QCAT and toxin proteolysis are concomitantly extracted from the gel. The adjustment of QCAT to 24 kDa was accomplished by incorporation of additional peptides potentially useful as quantification standards for other staphylococcal superantigenic toxins (see FIG. 1, other toxins not quantified in the present study). As the QCAT construct was solubilized in 1% SDS, it could not be captured on Strataclean resin. Consequently, it was introduced into the samples just before SDS-PAGE. The AQUA peptides standards which size imposes their addition after SDS-PAGE fractionation step, were added to the samples just before nanoLC-MS analysis as previously described [6].

Figure 6:
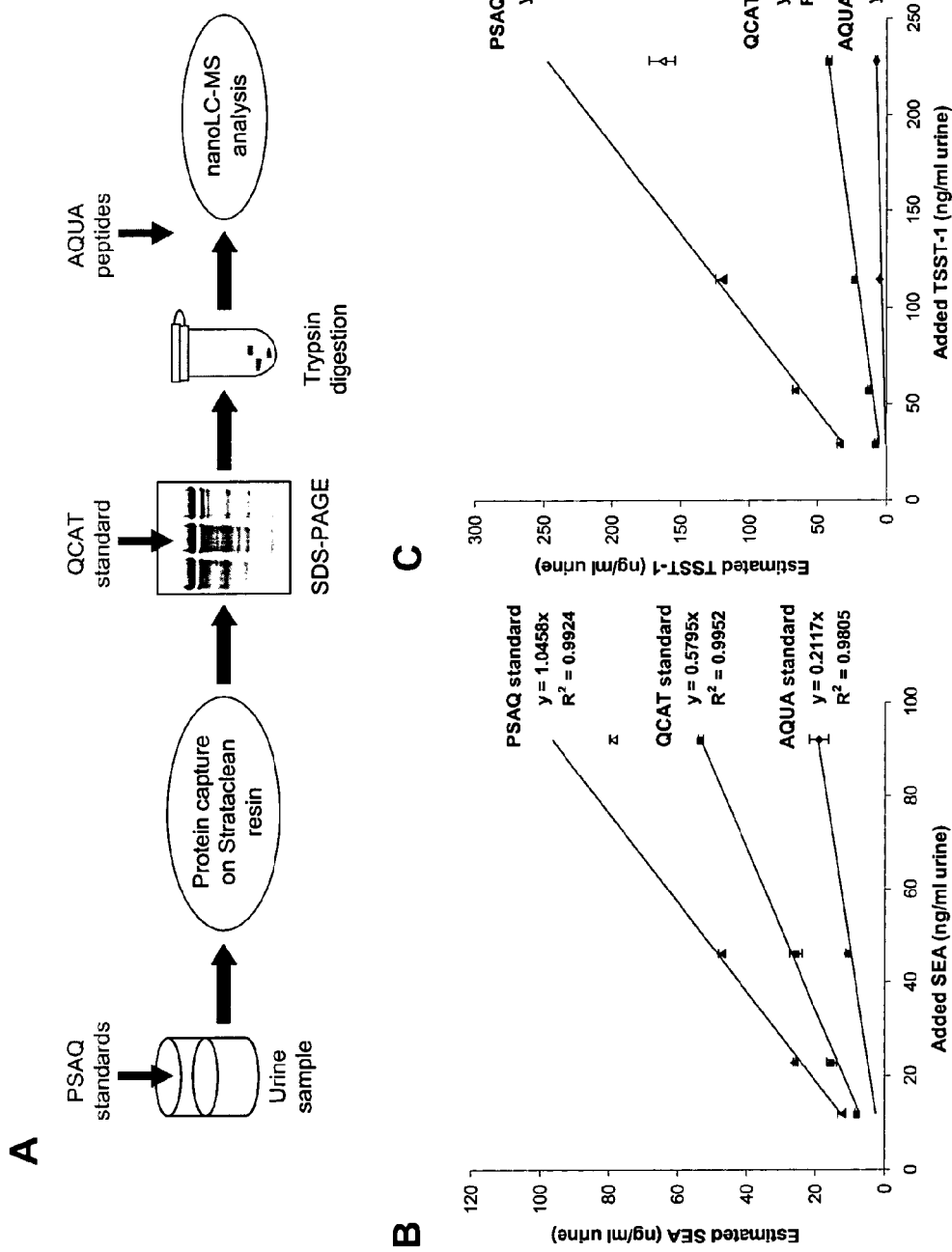

In comparison with the detection and quantification of SEA and TSST-1 in drinking water samples, lower sequence coverage was obtained in urine samples even when the PSAQ standards were used. As a matter of fact, a high background generated by urinary proteins prevented the detection of marker peptides QNTVPLETVK (SEQ ID NO.:2) and YNLYNSDVFDGK (SEQ ID NO.:3). In drinking water, toxins were quantitated down to respectively 7.7 pM (signal-to-noise ratio 75:1) for SEA and 3.8 pM (signal-to-noise ratio 15:1) for TSST-1. In contrast, the high protein complexity limited the quantitation sensitivity in urine to 0.4 nM (signal-to-noise ratio 35:1) for SEA and to 1.3 nM (signal-to-noise ratio 20:1) for TSST-1. FIG. 6 shows the estimates of SEA and TSST-1 amounts obtained with the different standards compared to the added amounts. Both AQUA and QCAT standardizations severely underestimated the toxin amounts in urine. This is due to addition of these standards at late stages of the analytical process (FIG. 6A). This emphasizes a major limitation of these strategies: their incompatibility with sample prefractionation. In contrast, PSAQ was the only quantitation strategy that allowed an accurate estimation of the toxins in this complex matrix (slope values=1.05 and 1.08 for SEA marker peptide NVTVQELDLQAR (SEQ ID NO.:1) and TSST-1 marker peptide LPTPIELPK (SEQ ID NO.:5), respectively) (FIGS. 6B and 6C).

Discussion

Concerning SEA and TSST-1 toxins, two AQUA peptides markedly underestimated their amounts (FIG. 2). Most likely, such an observation results from variabilities in trypsin digestion efficiency which are not accounted tbr when peptide standards are used. Thus, in view of our data, AQUA can be considered an exquisite quantification strategy for peptidomics [23]. However, for an accurate quantification of proteins, we believe that this strategy should be limited to low-complexity samples and to target proteins for which trypsin digestion efficiency has been characterized. In contrast with AQUA peptides, QCAT quantification gave more consistent results between the different marker peptides of a same protein (FIG. 4). When co-digested with the targets, QCAT also allowed correcting the variability of the protease activity induced by the digestion conditions (FIG. 3). However, essentially due to differential susceptibility to proteolysis, QCAT standard nonetheless led to an underestimation of the toxins (FIG. 4). Finally, the PSAQ strategy demonstrated a marked superiority over AQUA and QCAT approaches for toxin quantification in drinking water both in terms of inter-peptide consistency and accuracy (FIG. 5). The 26 to 42% overestimation of SEA abundance may originate from the adsorption of SEA PSAQ standard onto vials during the dilution process (final concentration before spiking: 10 nM). Accordingly, an excellent accuracy was observed for both SEA and TSST-1 titrations in urine samples (FIGS. 6B and 6C). In comparison with drinking water samples, the PSAQ standard solutions that were used for spiking urine samples were much more concentrated (200 nM), which may have prevented protein adsorption on vials. For both QCAT and AQUA strategies, the choice of the best peptide(s) to use for the quantification of any given protein is frequently based on an educated guess. Depending on the biological matrix and the prefractionation strategy, the choice of a single standard peptide can be inadequate (e.g. when the standard peptide is suppressed by other dominant peptides). The PSAQ strategy, which allows maximal protein coverage, circumvents these potential problems and provides a more robust quantification of the targets. As suggested by Anderson and Hunter [10] for small proteins, the difficulty to find a good peptide reporter can impose to swap trypsin for a distinct protease for peptide digestion. In a long term study, QCAT or AQUA standards freeze the choice of the quantification standards whereas PSAQ strategy opens the way to alternative peptide standards.

The possibility to integrate the prefractionation and digestion yields renders PSAQ strategy exquisitely attractive for the quantitative analysis of biomarkers in biological fluids. This improvement was demonstrated by the comparative quantification of SEA and TSST-1 toxins in a complex sample (e.g. urine) after Strataclean resin capture and SDS-PAGE prefractionation. Compared to drinking water samples, the protein complexity of urine samples generated high background and ionization competition that prevented MS-detection of several toxin marker peptides. With the remaining markers, both AQUA and QCAT severely underestimated the toxins amounts. The tendency of the AQUA strategy to underestimate protein targets was seriously aggravated after the SDS-PAGE prefractionation. This was also true for QCAT despite our SDS-PAGE-compatible design which allowed electrophoresis and co-digestion of QCAT with the toxin targets as well as the simultaneous extraction of labeled/ unlabeled peptides from the gel. Finally, only PSAQ standards gave reliable quantification after this prefractionation protocol. Even with the most powerful MS technologies, decomplexification often appears as a mandatory step before quantification of medium to low abundance proteins [10, 11]. Actually, AQUA quantifications are often realized on prefractionated protein samples [6, 21]. As illustrated in the present study, uncertainty on the yield of the target protein recovery due to these prefractionation steps can introduce important quantification biases that are efficiently corrected using PSAQ standards. This constitutes the major advantage of the PSAQ strategy over AQUA and QCAT approaches.

In conclusion, we have demonstrated the advantages of our PSAQ strategy over existing approaches for biomarkers absolute quantification in complex samples such as biological fluids. Considering the high sensitivity of MS analyses, a single medium-scale expression experiment provides sufficient amounts of a given PSAQ standard for thousands of quantification analyses. Moreover, simple quality controls such as SDS-PAGE coupled to quantitative fluorescent detection can be performed whenever required.

Example 2

Figure 12:
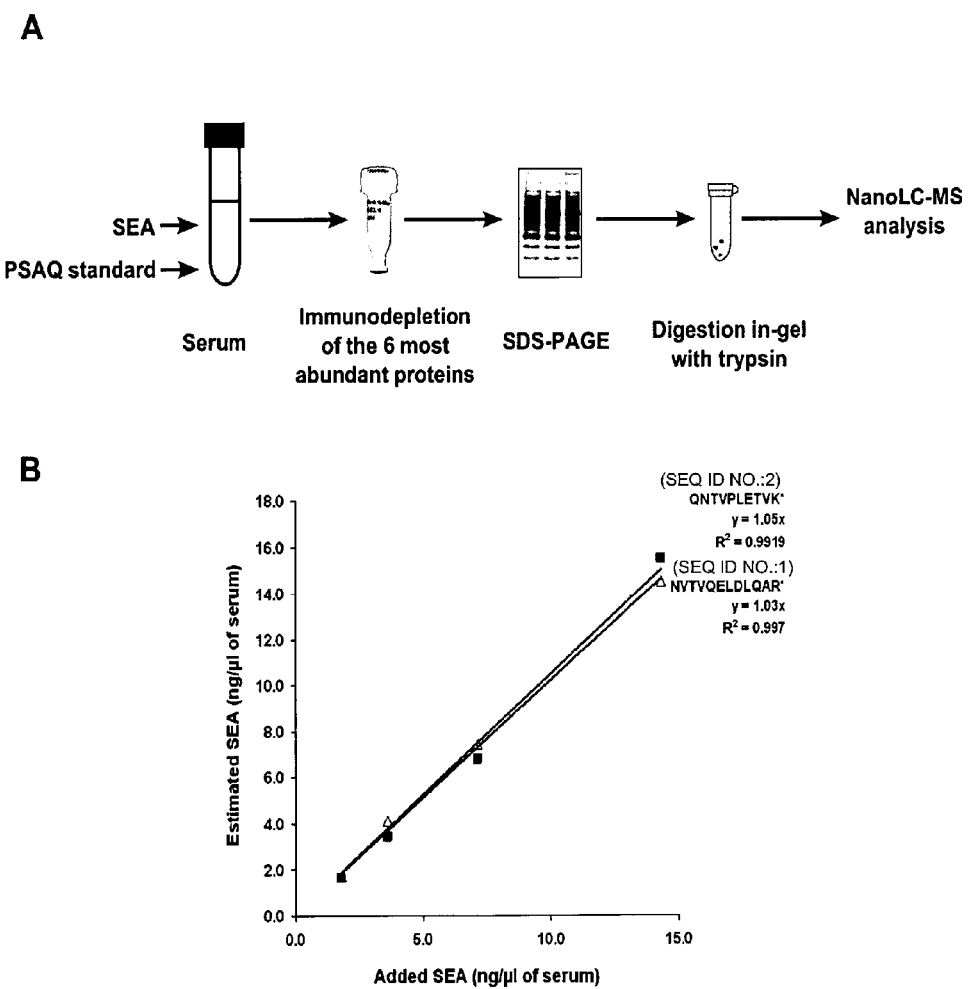

Absolute Quantification of Staphylococcal Enterotoxin A (SEA) in Serum Samples Using PSAQ Strategy (Serum samples were contaminated with SEA and spiked with a defined quantity of PSAQ standard (isotope-labeled SEA). The samples were depleted of the 6 most-abundant proteins using a MARS spin cartridge (Agilent Technologies) and were submitted to SDS-PAGE. Following in-gel digestion with trypsin, peptides were extracted and analyzed using nanoLC-MS (FIG. 12A). SEA quantification was derived from the extracted ion chromatograms of unlabeled/labeled peptide pairs (QNTVPLETVK (SEQ ID NO.:2) and NVTVQFLDLQAR (SEQ ID NO.:1) peptide pairs). For both proteotypic peptide pair considered, the estimated SEA quantities in serum samples was plotted against the spiked quantity (FIG. 12B).

Example 3

Protein Standard Absolute Quantification (PSAQ) for Improved Investigation of Staphylococcal Food Poisoning Outbreaks Abstract Staphylococcal enterotoxins are major causing agents of food-borne diseases. Their detection in food remnants for risk assessment or food poisoning outbreaks investigation suffers from a lack in comprehensive immunological tools. In this study, we demonstrate that the combination of immunocapture and PSAQ strategy, which uses isotope-labeled enterotoxins as internal standards for MS-based analysis, is powerful to specifically identify and quantify these contaminating agents in food matrices. This approach significantly improves the elucidation of staphylococcal food poisoning outbreaks.

We combined PSAQ strategy and immunocapture for the detection and absolute quantification of traces of staphylococcal enterotoxin A (SEA), a major agent of food poisoning, in contaminated food samples.

Staphylococcal food poisoning (SFP) is a common food-borne disease resulting from ingestion of staphylococcal enterotoxins (SEs) preformed in food by *Staphylococcus aureus* strains. In the United States, SEs are responsible for 185,000 annual cases of food poisoning. In France, staphylococcal enterotoxins represent the second cause of food-borne diseases after *Salmonella*. To date, nineteen staphylococcal enterotoxins and related toxins ("enterotoxin-like" proteins) have been described. Strains isolated from food involved in SFP mainly produce SEA and to a lesser extent SED, SEB and SEC. However, due to the lack of specific diagnosis tools against numerous SEs and related toxins, many SEP outbreaks remain unsolved. SFP is clinically characterized by gastroenteritis occurring between one to eight hours after food consumption. The biological diagnosis of SFP is conclusive when SEs are detected in food remnants. The detection of SEs is classically performed using immunological techniques (ELISA) [Hennekinne et al., *J AOAC Int* 2007, 90, 756-764]. However, the immunological detection of SEs displays major drawbacks. First, due to the high sequence and structural homology between SEs, very few specific antibodies are available. Second, the complexity of food matrices often generates non-specific reactions [Hennekinne et al., *J AOAC Int* 2007, 90, 756-764]. Finally, the well-known IgG-binding staphylococcal protein A is co-secreted in food with SEs and can interfere with the assay. Consequently, commercial kits are available only for the detection of five enterotoxins (SEA to SEE) and suffer from serious limitations in terms of sensitivity, specificity and suitability for complex food matrices analysis.

We thus investigated the potential of the PSAQ method as an alternative to ELISA for SFP outbreaks characterization. Semi-hard cow-milk cheese was first chosen as a model, as it represents a high risk for *S. aureus* growth and staphylococcal enterotoxins (SEs) production. The cheese model was manufactured in the "Lactic Acid Bacteria and Opportunistics Pathogens" laboratory of the French National Institute for Agricultural Research (Jouy en Josas, France). A SEA producing *S. aureus* strain was inoculated into the milk before processing. According to the official procedure for diary products control, a piece of cheese (25 g) was homogenized, depleted from caseins and the extract was concentrated by dialysis against polyethylene glycol (see reference Hennekinne et al., *J AOAC Int* 2007, 90, 756-764 for more details). This extract was investigated in parallel using a reference quantitative ELISA or using our MS-based PSAQ method. For PSAQ analysis, the cheese extract was spiked with 100 ng of SEA PSAQ-standard isotopically labeled with $[^{13}C_6, ^{15}N_2]$ L-lysine and $[^{13}C_6, ^{15}N_4]$ L-arginine. The spiked cheese extract was passed through an immunoaffinity column (Biocontrol Systems, Lyon, France) designed to capture five enterotoxins (SEA to SEE). The eluate was collected and submitted to short-run SDS-PAGE. The 25-30 kDa region of the gel, containing the endogenous enterotoxin and its isotope-labeled counterpart, was excised and submitted to digestion with trypsin. The proteolytic peptides were extracted and analyzed in nanoLC-MS using a QToF mass spectrometer (Waters, Milford, Mass., USA). Whereas the immunoaffinity column allows a large-spectrum enterotoxin capture, MS analysis allows a highly specific assignment of enterotoxins through the identification of peptides unique to each protein (i.e. proteotypic peptides). One such proteotypic peptide (peptide NVTVQELDLQAR (SEQ ID NO.:1)) was detected in the cheese sample, specifically indicating the presence of endogenous SEA. Quantification was performed by comparing the integrated peaks of endogenous/labeled peptide extracted ion chromatograms (MassLynx software, Waters). The endogenous SEA was detected at 2.5±0.2 ng/g of cheese (n=3) which was consistent with the ELISA estimate (2.9±0.3 ng/g; n=3).

Figure 9:
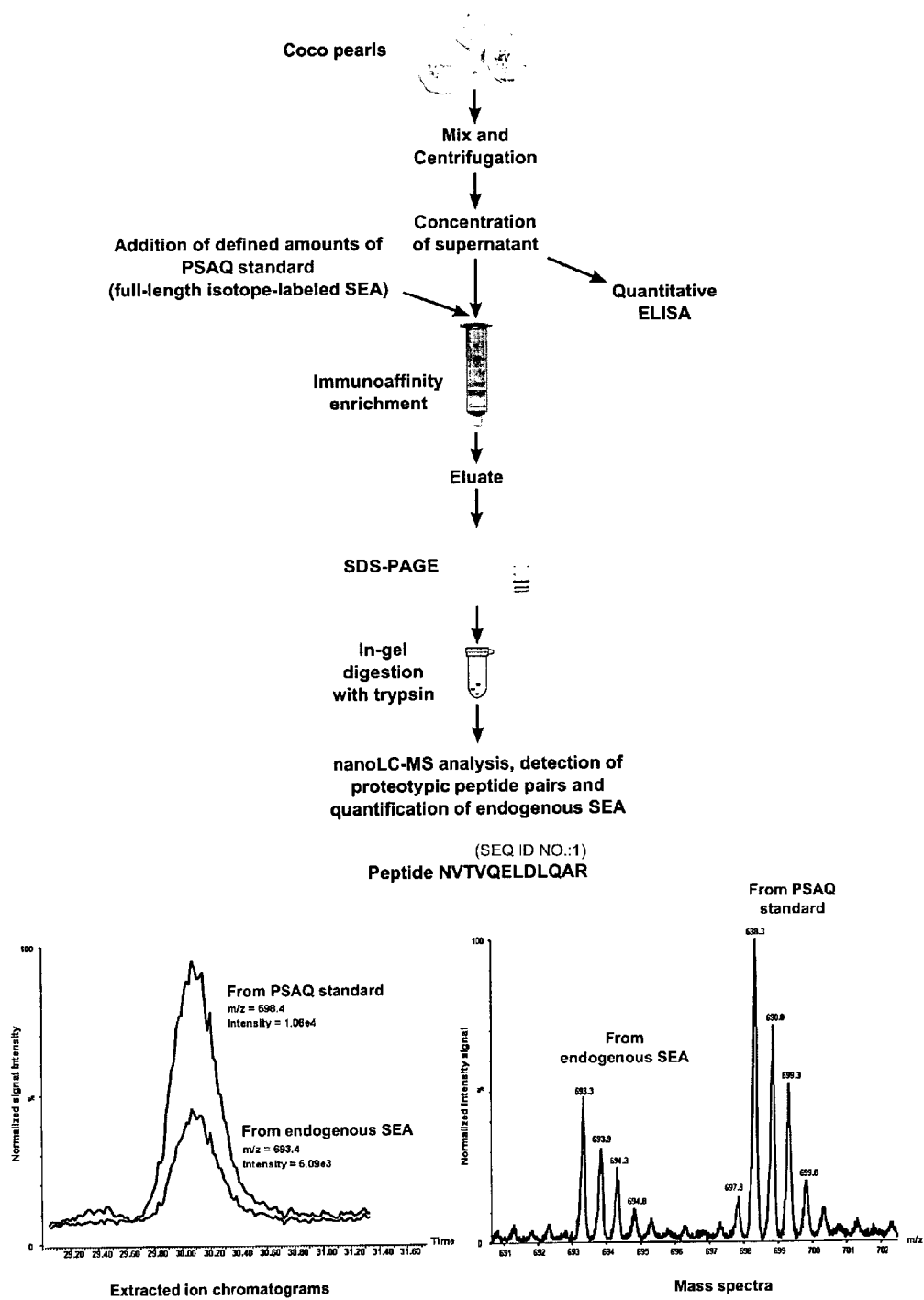

To go beyond this proof of concept, we applied the same PSAQ strategy to investigate a to naturally contaminated food matrix. A Chinese dessert (coco-pearls) involved in a food poisoning outbreak in France in 2006 (11 patients declared), was collected by the French Agency for Food Safety (AFSSA), From this sample, AFSSA isolated a *Staphylococcus aureus* strain carrying the gene encoding SEA. To confirm the presence of SEA at the protein level, a coco-pearl sample (25 g) was homogenized, centrifuged and the supernatant was concentrated by dialysis against polyethylene glycol. The extract was tested concomitantly using ELISA or PSAQ method. Before MS analysis, the extract was spiked with 100 ng of SEA PSAQ standard, immunoenriched, and submitted to SDS-PAGE and trypsin digestion. The proteolytic peptides were analyzed with nanoLC-MS analysis on a Q-ToF (FIG. 9). Two proteotypic peptides specifically indicated the presence of endogenous SEA (peptides YNLYNSDVFDGK (SEQ ID NO.:3) and NVTVQELDLQAR (SEQ ID NO.:1)). Using these peptides, SEA was quantified down to 1.47±0.05 ng/g of food (n=3). This result was in agreement with the 1.3±0.2 ng/g (n=3) ELISA estimate obtained from the same sample and was also consistent with the symptoms declared (toxic dose=40 ng according to Ikeda et al. Appl Environ Microbiol 2005, 71, 2793-2795).

In this work, we have harnessed the power of the PSAQ strategy for the specific detection and quantification of staphylococcal enterotoxin A in food matrices. The use of the isotope dilution principle with PSAQ standards allows an accurate quantification. Accordingly, the PSAQ analysis and the established ELISA gave comparable estimates and displayed similar sensitivity. On top, PSAQ methodology displayed an unrivalled detection specificity related to proteotypic peptides detection. Thus, this methodology, which can be easily extended to other SEs, represents an attractive alternative to immunoassays.

To perform a relevant comparison with the ELISA estimates, we had to spike the PSAQ standard in the polyethylene glycol-concentrated food extracts prepared for ELISA testing. However, in contrast to the ELISA approach, PSAQ standards can be added in the food homogenate at the very beginning of the analytical process, enabling to assess the eventual enterotoxin losses during the extraction/concentration procedure. This simple modification would further increase the accuracy of toxin quantification in food.

The present experiments, performed on a Q-ToF mass spectrometer, gave a sensitivity limit comparable to that of the established commercial ELISA kits. However, the use of the Multiple Reaction Monitoring (MRM) method on a triple quadrupole instrument for MS analysis is expected to further lower the detection sensitivity by a factor of at least ten. This mode of analysis should also increase the sequence coverage for identification and quantification.

At present, we are synthesizing a panel of isotope-labeled full-length SEs to constitute a PSAQ standard library dedicated to SFP investigation. These enterotoxin PSAQ standards will be spiked simultaneously in naturally contaminated samples. After immunocapture, they will allow a multiplex detection and quantification of the incriminated enterotoxin(s).

In conclusion, PSAQ strategy represents the ideal alternative methodology to investigate SPP outbreaks unsolved with the existing immunological tools. This allows the evaluation of the digestive pathogenicity of poorly characterized staphylococcal enterotoxins.

Example 4

A "Phospho-PSAQ" Strategy for the Quantification of Protein Phosphorylations

Figure 10:
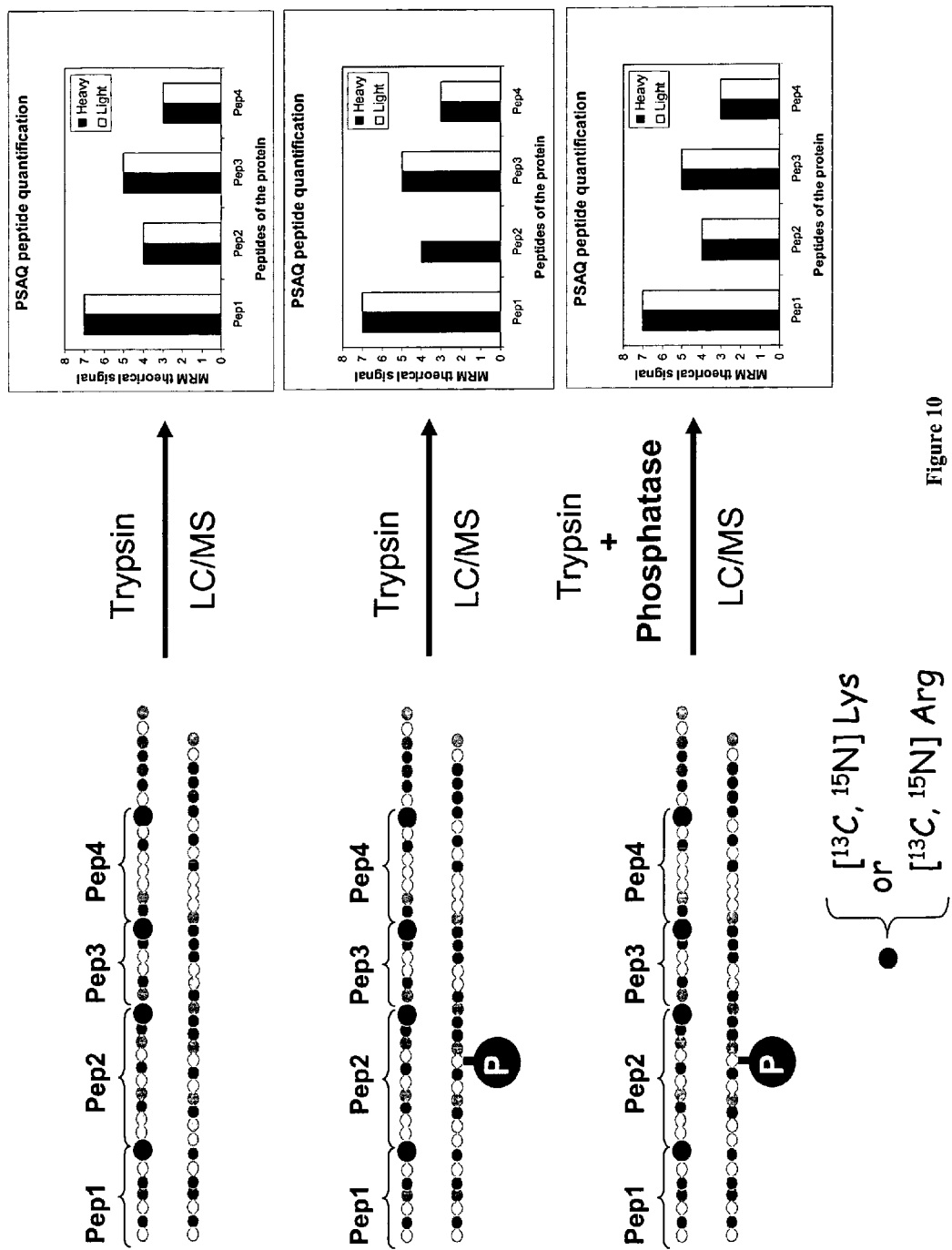

A strategy can allow the adaptation of the PSAQ strategy to the quantification of proteins presenting post-translational modifications (PTM), phosphorylation for example. Due both to the lability of phosphorylations and to the poor detection of phosphorylated peptides with conventional mass spectrometry, phospho-proteomic may require specific protocols for phospho-peptides enrichment and dedicated mass spectrometry strategies. Typically LC-MRM (Multiple Reaction Monitoring) may be used. With PSAQ, we can estimate the absolute concentrations of the different MS-observable peptides of a given protein. In the absence of phosphorylation (or more generally any PTM), all these peptides should be in equimolar concentration (FIG. 10). A post-translational modification will introduce a change in this isostoichiometric distribution. This change can result from any peptide modification. Thus, a second MS analysis of the peptide distribution after phosphatase suppression of all the phosphorylations may confirm/infirm the presence of a phosphorylation. This method allows both the discovery and the quantification of a phosphorylated peptide in a targeted protein. If the phosphatase treatment is carried out in the presence of $H_2^{18}O$, it can even allow the precise identification of the phosphorylated amino-acid residues.

Example 5

"Glyco-PSAQ": Adapting PSAQ for the Quantification of Glycosylated Proteins

Figure 11:
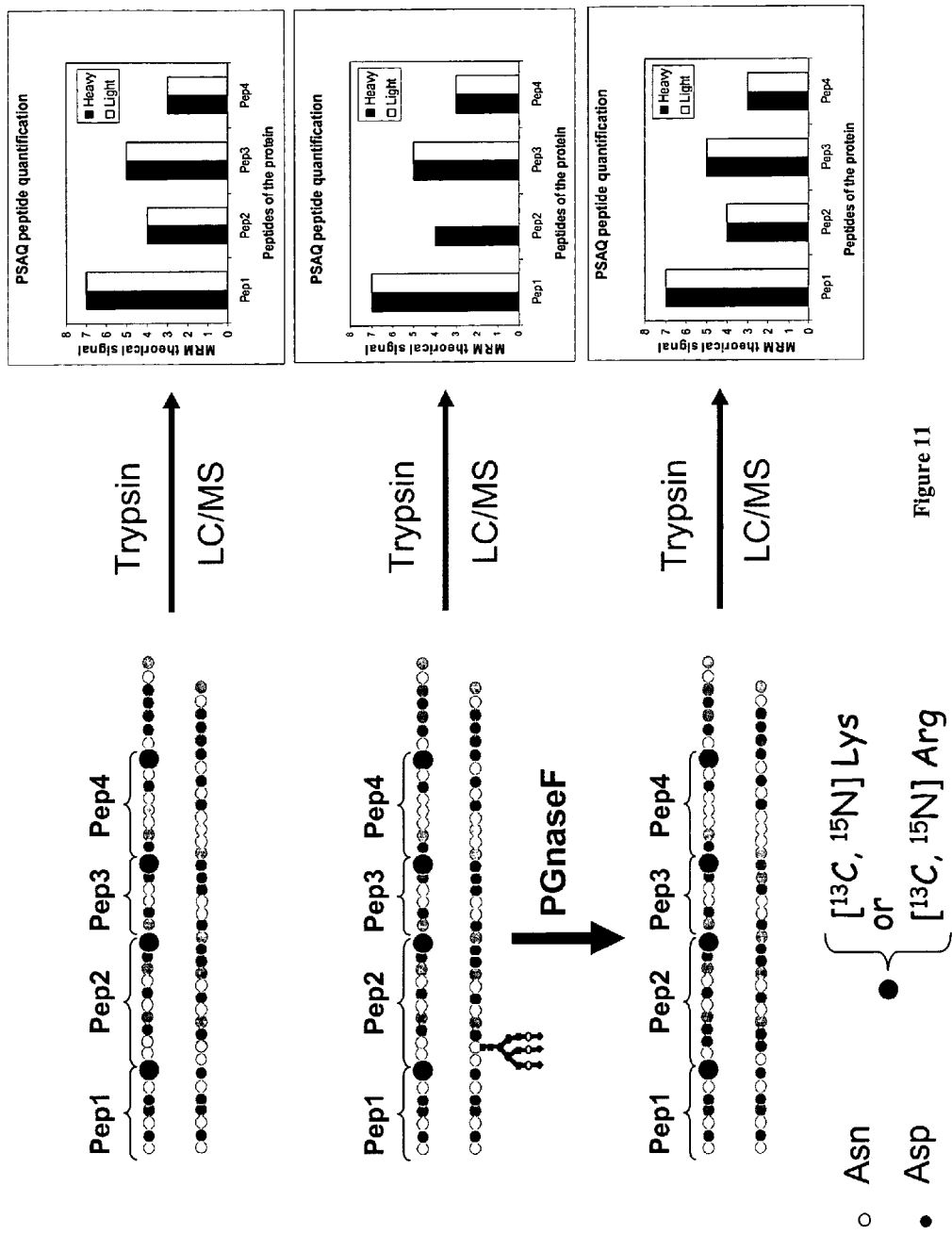

Many proteins, among which established and potential biomarkers, are glycosylated. This is the case for the cancer biomarkers Carcino-Embryonic Antigen (CEA) or Prostate Specific Antigen (PSA). We have conceived a strategy to adapt PSAQ quantification to glycosylated proteins. In biological samples the glycosylation of a given protein is often heterogenous. This is well illustrated by the broadening of glycosylated proteins bands observed on SDS-PAGE. The biochemical heterogeneity of protein glycosylation can flaw LC-MS quantifications if a differentially glycosylated protein behaves as an heterogenous population in the biochemical steps preceding LC-MS analysis. As clearly evidenced on SDS-PAGE, enzymatic deglycosylation of proteins is a good way to retrieve homogeneity. Furthermore, from the example of endo-lysosomal proteins it can be appreciated that glycosylation is a good shield against protease attacks. This may also differentially affect trypsin digestion efficiency. We thus consider that treatment of the biological material with an efficient N-glycosidase like PGNase-F should be included early in the experimental flowchart of the PSAQ quantification protocol dedicated to glycosylated proteins. However, this deglycosylation step potentially introduces three limitations: i) for quantification, the specific deglycosylation yield of a given protein should be evaluated, ii) PGNase-F deglycosylation transforms N-glycosylated asparagines into aspartic acid. This point should be taken into account in the design of a dedicated PSAQ, iii) deglycosylation generally decreases the overall water-solubility of proteins. This can be corrected by the choice of appropriate solubilisation buffers. Considering a glycosylated protein to be quantified and taking into account these limitations, the following workflow can be advantageously established: a PSAQ standard is designed with replacement of the asparagines by aspartic acids at known N-glycosylation points reported. Using this PSAQ standard and the extensively deglycosylated natural protein, the absolute amount of the deglycosylated peptides are compared to that of other unglycosylated peptides of the protein. If deglycosylation is complete, all the peptides should be equimolar (cf. FIG. 11).

REFERENCES

Throughout this application, various references describe the state of the art to which this invention pertains. The disclosures of these references are hereby incorporated by reference into the present disclosure.

1. Aebersold, R. (2003) Constellations in a cellular universe. *Nature*, 422, 115-116.
2. Lu, P., Vogel, C., Wang, R., Yao, X. and Marcotte, E. M. (2007) Absolute protein expression profiling estimates the relative contributions of transcriptional and translational regulation. *Nat Biotechnol*, 25, 117-124.
3. Mallick, P., Schirle, M., Chen, S. S. Flory, M. R., Lee, H., Martin, D., Ranish, J., Raught, B., Schmitt, R., Werner, T., Kuster, B. and Aebersold, R. (2007) Computational prediction of proteotypic peptides for quantitative proteomics. *Nat Biotechnol*, 25, 125-131.
4. Tai, S. S., Bunk, D. M., White, E. t. and Welch, M. J. (2004) Development and evaluation of a reference measurement procedure for the determination of total 3,3',5-triiodothyronine in human serum using isotope-dilution liquid chromatography-tandem mass spectrometry. *Anal Chem*, 76, 5092-5096.
5. Gerber, S. A., Rush, J., Stemman, O., Kirschner, M. W. and Gygi, S. P. (2003) Absolute quantification of proteins and phosphoproteins from cell lysates by tandem MS. *Proc Natl Acad Sci USA*, 100, 6940-6945.
6. Kirkpatrick, D. S., Gerber, S. A. and Gygi, S. P. (2005) The absolute quantification strategy: a general procedure for the quantification of proteins and post-translational modifications. *Methods*, 35, 265-273.
7. Stemmann, O., Zou, H., Gerber, S. A., Gygi, S. P. and Kirschner, M. W. (2001) Dual inhibition of sister chromatid separation at metaphase. *Cell*, 107, 715-726.
8. Barr, J. R., Maggio, V. L., Patterson, D. G., Jr., Cooper, G. R., Henderson, L. O., Turner, W. E., Smith, S. J., Hannon, W. H., Needham, L. L. and Sampson, E. J. (1996) Isotope dilution-mass spectrometric quantification of specific proteins: model application with apolipoprotein A-I. *Clin Chem*, 42, 1676-1682.
9. Beynon, R. J., Doherty, M. K., Pratt, J. M. and Gaskell, S. J. (2005) Multiplexed absolute quantification in proteomics using artificial QCAT proteins of concatenated signature peptides. *Nat Methods*, 2, 587-589.
10. Anderson, L. and Hunter, C. L. (2006) Quantitative mass spectrometric multiple reaction monitoring assays for major plasma proteins. *Mol Cell Proteomics*, 5, 573-588.
11. Shen, Y., Kim, J., Strittmatter, E. F., Jacobs, J. M., Camp, D. G., 2nd, Fang, R., Tolie, N., Moore, R. J. and Smith, R. D. (2005) Characterization of the human blood plasma proteome. *Proteomics*, 5, 4034-4045.
12. McCormick, J. K., Yarwood, J. M. and Schlievert, P. M. (2001) Toxic shock syndrome and bacterial superantigens: an update. *Annu Rev Microbiol*, 55, 77-104.
13. Dinges, M. M., Orwin, P. M. and Schlievert, P. M. (2000) Exotoxins of *Staphylococcus aureus*. *Clin Microbial Rev*, 13, 16-34.
14. Ferry, T., Thomas, D., Genestier, A. L., Bes, M., Lina, G., Vandenesch, F. and Etienne, J. (2005) Comparative prevalence of superantigen genes in *Staphylococcus aureus* isolates causing sepsis with and without septic shock. *Clin Infect Dis*, 41, 771-777.
15. Thomas, D., Chou, S., Dauwalder, O. and Lina, G. (2007) Diversity in *Staphylococcus aureus* Enterotoxins. *Chem. Immunol Allergy*, 93, 2441.
16. Torizawa, T., Shimizu, M., Taoka, M., Miyano, H. and Kainosho, M. (2004) Efficient production of isotopically labeled proteins by cell-free synthesis: a practical protocol. *J Biomol NMR*, 30, 311-325.
17. Nishihara, J. C. and Champion, K. M. (2002) Quantitative evaluation of proteins in one- and two-dimensional polyacrylamide gels using a fluorescent stain. *Electrophoresis*, 23, 2203-2215.
18. Jaquinod, M., Villiers, F., Kieffer-Jaquinod, S., Hugouvieux, V., Bruley, C., Garin, J. and Bourguignon, J. (2007) A Proteomics Dissection of *Arabidopsis thaliana* Vacuoles Isolated from Cell Culture. *Mol Cell Proteomics*, 6, 394-412.
19. Kigawa, T., Muto, Y. and Yokoyama, S. (1995) Cell-free synthesis and amino acid-selective stable isotope labeling of proteins for NMR analysis. *J Biomol NMR*, 6, 129-134.
20. Taussig, M. J., Stoevesandt, O., Borrebaeck, C. A., Bradbury, A. R., Cahill, D., Cambillau, C., de Daruvar, A., Dubel, S., Eichler, J., Frank, R., Gibson, T. J., Gloriam, D., Gold, L., Herberg, F. W., Hermjakob, H., Hoheisel, J. D., Joos, T. O., Kallioniemi, O., Koegl, M., Konthur, Z., Korn, B., Kremmer, E., Krobitsch, S., Landegren, U., van der Maarel, S., McCafferty, J., Muyldermans, S., Nygren, P. A., Paley, S., Pluckthun, A., Polic, B., Przybylski, M., Saviranta, P., Sawyer, A., Sherman, D. J., Skerra, A., Templin, M., Ueffing, M. and Uhlen, M. (2007) ProteomeBinders: planning a European resource of affinity reagents for analysis of the human proteome. *Nat Methods*, 4, 13-17.
21. Rifai, N., Gillette, M. A. and Carr, S. A. (2006) Protein biomarker discovery and validation: the long and uncertain path to clinical utility. *Nat Biotechnol*, 24, 971-983.
22. Ong, S. E. and Mann, M. (2005) Mass spectrometry-based protemnics turns quantitative. *Nat Chem Biol*, 1, 252-262.
23. Wei, H., Nolkrantz, K., Parkin, M. C, Chisolm, C. N., O'Callaghan, J. P. and Kennedy, R. T. (2006) Identification and quantification of neuropeptides in brain tissue by capillary liquid chromatography coupled off-line to MALDI-TOF and MALDI-TOF/TOF-MS. *Anal Chem*, 78, 4342-4351.
24. Barnidge, D. R., Goodmanson, M. K., Klee, G. G. and Muddiman, D. C. (2004) Absolute quantification of the model biomarker, prostate-specific antigen in serum by LC-MS/MS using protein cleavage and isotope dilution mass spectrometry. *J Proteome Res*, 3, 644-652.
25. Cheng, D., Hoogenraad, C. C., Rush, J., Ramm, E., Schlager, M. A., Duong, D. M., Xu, P., Wijayawardana, S. R., Hanfelt, J., Nakagawa, T., Sheng, M. and Peng, J. (2006) Relative and absolute quantification of postsynaptic density proteome isolated from rat forebrain and cerebellum. *Mol Cell Proteomics*, 5, 1158-1170.
26. Beynon, R. J. and Pratt, J. M. (2005) Metabolic labeling of proteins for proteomics. *Mol Cell Proteomics*, 4, 857-872.
27. Muchmore, D. C., McIntosh, L. P., Russell, C. B., Anderson, D. E. and Dahlquist, F. W. (1989) Expression and nitrogen-15 labeling of proteins for proton and nitrogen-15 nuclear magnetic resonance. *Methods Enzymol,* 177, 44-73.

28. Vinarov, D. A., Lytle, B. L., Peterson, F. C., Tyler, E. M., Volkman, B. F. and Markley, J. L. (2004) Cell-free protein production and labeling protocol for NMR-based structural proteomics. *Nat Methods,* 1, 149-153.
29. Kuhn, E., Wu, J., Karl, J., Liao, H., Zolg, W. and Guild, B. (2004) Quantification of C-reactive protein in the serum of patients with rheumatoid arthritis using multiple reaction monitoring mass spectrometry and 13C-labeled peptide standards. *Proteomics,* 4, 1175-1186.
30. Fischer, A., von Eiff, C., Kuczius. T., Omoe, K., Peters, G. and Becker, K. (2007) A quantitative real-time immuno-PCR approach for detection of *staphylococcal enterotoxins. J Mol Med*, Epub ahead of print.
31. Callahan, J. H., Shefcheck, K. J., Williams, T. L. and Musser, S. M. (2006) Detection, confirmation, and quantification of staphylococcal enterotoxin B in food matrixes using liquid chromatography-mass spectrometry. *Anal Chem.* 78, 1789-1800.
32. Domon, B. and Aebersold, R. (2006) Mass spectrometry and protein analysis. *Science,* 312, 212-217.
33. Unwin, R. D. Griffiths, J. R., Leerentz, M. K., Grallert, A., Hagan, I. M. and Whetton, A. D. (2005) Multiple reaction monitoring to identify sites of protein phosphorylation with high sensitivity. *Mol Cell Proteomics,* 4, 1134-1144.
34. Thomas, D. Y., Jarraud, S., Lemercier, B. Cozon, G., Echasserieau, K., Etienne, J., Gougeon, M. L., Lina, G. and Vandenesch, F. (2006) Staphylococcal enterotoxin-like toxins U2 and V, two new staphylococcal superantigens arising from recombination within the enterotoxin gene cluster. *Infect Immun,* 74, 4724-4734.
35. Stevens, R. C., Yokoyama, S. and Wilson, I. A. (2001) Global efforts in structural genomics. *Science,* 294, 89-92.
36. Mischak H., A. R., Banks R. E., Conaway M., Coon J., Dominiczak A., Ehrich J. H. H., Fliser D., Girolami M., Hermjakob H., Hochstrasser D., Jankowski J., Julian B. A., Kolch W., Massy Z. A., Neusuess C., Novak J., Peter K., Rossing K., Schanstra J., Semmes O. J., Theodorescu D., Thongboonkerd V., Weissinger E. M., Van Eyk J. E., and Yamamoto T. (2007) Clinical proteomics: A need to define the field and to begin to set adequate standards. *Proteomics Clinical Applications,* 1, 148-156.

The invention claimed is:

1. A method for quantifying a target polypeptide in a sample comprising the steps of:
    (a) providing a sample containing a full length target polypeptide to be quantified;
    (b) adding a known quantity of an in vitro synthesized, isotope labeled full length homolog of said full length target polypeptide wherein the homolog has the identical amino acid sequence as the full length target polypeptide to be quantified except that all lysine residues in said homolog are labeled with $^{13}C$ and/or $^{15}N$ such that all the lysine residues in said homolog are [$^{13}C$ and/or $^{15}N$]-lysine and all arginine residues in said homolog are labeled with $^{13}C$ and/or $^{15}N$ such that all the arginine residues in said homolog are [$^{15}N$ and/or $^{13}C$]-arginine thereby generating a spiked sample comprising the polypeptide to be quantified and the isotope labeled homolog;
    (c) treating the spiked sample with trypsin to digest the polypeptide and the isotope labeled homolog in said spiked sample to generate a plurality of proteolytic peptides;
    (d) analysing the proteolytic peptides generated in step c) by mass spectrometry (MS);
    (e) determining a ratio of an isotope-labeled proteolytic peptide to the corresponding unlabeled proteolytic peptide; and
    (f) calculating from the ratio and the known quantity of the isotope-labeled target polypeptide, the quantity of the target polypeptide in the sample.

2. A method according to claim 1, wherein the isotope-labeled homolog is isotope-labeled by using cell-free extracts.

3. A method for quantifying a target polypeptide in a sample comprising the steps of:
    (a) providing a sample containing a full length target polypeptide to be quantified;
    (b) adding a known quantity of an in vitro synthesized, isotope labeled full length homolog of said full length target polypeptide wherein the isotope labeled full length homolog has the identical amino acid sequence as the full length target polypeptide to be quantified except that all lysine residues in said homolog are labeled with either $^{13}C$ and/or $^{15}N$, such that all the lysine residues in the homolog are [$^{13}C$ and/or $^{15}N$] -lysine, thereby generating a spiked sample comprising the polypeptide to be quantified and the isotope labeled homolog;
    (c) treating the spiked sample with endoproteinase Lys-C to digest the polypeptide and the isotope labeled homolog in said spiked sample to generate a plurality of proteolytic peptides;
    (d) analysing the proteolytic peptides generated in step c) by mass spectrometry (MS);
    (e) determining a ratio of an isotope-labeled proteolytic peptide to the corresponding unlabeled proteolytic peptide; and
    (f) calculating from the ratio and the known quantity of the isotope-labeled target polypeptide, the quantity of the target polypeptide in the sample.

4. A method according to claim 1, wherein the target polypeptide is a biomarker, a bacterial protein, a viral protein, a plant protein, a yeast protein, a mold protein, a fungal protein, an animal protein or a toxin.

5. A method according to claim 4, wherein the target polypeptide is a superantigenic toxin.

6. A method according to claim 1, wherein the sample is obtained from a biological fluid, a tissue homogenate, a cells homogenate, a cell culture supernatant, water, food or a bio-collection fluid.

7. A method according to claim 1, wherein the method comprises at least one fractionation steps between step (b) and step (d).

8. A method according to claim 1, wherein the target polypeptide and its isotope-labeled homolog are either reduced and alkylated or oxidized by an oxidizing agent in order to avoid difference of oxidation state between the target polypeptide and its isotope-labeled homolog.

9. A method according to claim 1, wherein said target polypeptide carries at least one post-translational modifications, and wherein said method comprises an additional step between step (a) and step (c) of removing said at least one post-translational modifications of said target polypeptide, and wherein said isotope-labeled target polypeptide is an isotope-labeled target polypeptide obtained by the step of removing said at least one post-translational modifications of said target polypeptide.

10. A method according to claim 3, wherein the isotope-labeled homolog is isotope-labeled by using cell-free extracts.

11. A method according to claim 3, wherein the target polypeptide is a biomarker, a bacterial protein, a viral protein, a plant protein, a yeast protein, a mold protein, a fungal protein, an animal protein or a toxin.

12. A method according to claim 11, wherein the target polypeptide is a superantigenic toxin.

13. A method according to claim 3, wherein the sample is obtained from a biological fluid, a tissue homogenate, a cells homogenate, a cell culture supernatant, water, food or a bio-collection fluid.

14. A method according to claim 3, wherein the method comprises at least one fractionation steps between step (b) and step (d).

15. A method according to claim 3, wherein the target polypeptide and its isotope-labeled homolog are either reduced and alkylated or oxidized by an oxidizing agent in order to avoid difference of oxidation state between the target polypeptide and its isotope-labeled homolog.

16. A method according to claim 3, wherein said target polypeptide carries at least one post-translational modifications, and wherein said method comprises an additional step between step (a) and step (c) of removing said at least one post-translational modifications of said target polypeptide, and wherein said isotope-labeled target polypeptide is an isotope-labeled target polypeptide obtained by the step of removing said at least one post-translational modifications of said target polypeptide.

* * * * *

SEQUENCE LISTING

```
<160> NUMBER OF SEQ ID NOS: 25

<210> SEQ ID NO 1
<211> LENGTH: 12
<212> TYPE: PRT
<213> ORGANISM: Artificial Sequence
<220> FEATURE:
<223> OTHER INFORMATION: fragment

<400> SEQUENCE: 1

Asn Val Thr Val Gln Glu Leu Asp Leu Gln Ala Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: fragment

<400> SEQUENCE: 2

Gln Asn Thr Val Pro Leu Glu Thr Val Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: fragment

<400> SEQUENCE: 3

Tyr Asn Leu Tyr Asn Ser Asp Val Phe Asp Gly Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: fragment
```

<400> SEQUENCE: 4

His Gln Leu Thr Gln Ile His Gly Leu Tyr Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: fragment

<400> SEQUENCE: 5

Leu Pro Thr Pro Ile Glu Leu Pro Leu Lys
1               5                   10

<210> SEQ ID NO 6
<211> LENGTH: 22
<212> TYPE: PRT
<213> ORGANISM: Artificial Sequence
<220> FEATURE:
<223> OTHER INFORMATION: fragment

<400> SEQUENCE: 6

Asn Thr Asp Gly Ser Ile Ser Leu Ile Ile Phe Pro Ser Pro Tyr Tyr
1               5                   10                  15

Ser Pro Ala Phe Thr Lys
            20

<210> SEQ ID NO 7
<211> LENGTH: 12
<212> TYPE: PRT
<213> ORGANISM: Artificial Sequence
<220> FEATURE:
<223> OTHER INFORMATION: fragment

<400> SEQUENCE: 7

Gln Leu Ala Ile Ser Thr Leu Asp Phe Glu Ile Arg
1               5                   10

<210> SEQ ID NO 8
<211> LENGTH: 55
<212> TYPE: DNA
<213> ORGANISM: Artificial Sequence
<220> FEATURE:
<223> OTHER INFORMATION: primer

<400> SEQUENCE: 8
ggggacaagt ttgtacaaaa aagcaggcta tattcaacca tgggtgcgaa agtta          55

<210> SEQ ID NO 9
<211> LENGTH: 53
<212> TYPE: DNA
<213> ORGANISM: Artificial Sequence
<220> FEATURE:
<223> OTHER INFORMATION: primer

<400> SEQUENCE: 9
ggggaccact ttgtacaaga aagctgggta tgacaatata cccgggacga cct            53

<210> SEQ ID NO 10
<211> LENGTH: 30
<212> TYPE: DNA
<213> ORGANISM: Artificial Sequence
<220> FEATURE:
<223> OTHER INFORMATION: primer

```
<400> SEQUENCE: 10
tgaccccgcg gaagcgagaa aagcgaagaa                                        30

<210> SEQ ID NO 11
<211> LENGTH: 43
<212> TYPE: DNA
<213> ORGANISM: Artificial Sequence
<220> FEATURE:
<223> OTHER INFORMATION: primer

<400> SEQUENCE: 11
taaattcccg ggttaacttg tatataaata tatatcaata tgc                         43

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
tgaccccgcg gatctacaaa cgataatata aggat                                  36

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
atttaacccg ggttaattaa tttctgcttc tatagtttt                              39

<210> SEQ ID NO 14
<211> LENGTH: 8
<212> TYPE: PRT
<213> ORGANISM: Artificial Sequence
<220> FEATURE:
<223> OTHER INFORMATION: fragment

<400> SEQUENCE: 14

Leu Gly Asn Tyr Asp Asn Val Arg
1               5

<210> SEQ ID NO 15
<211> LENGTH: 14
<212> TYPE: PRT
<213> ORGANISM: Artificial Sequence
<220> FEATURE:
<223> OTHER INFORMATION: fragment

<400> SEQUENCE: 15

Val Leu Tyr Asp Asp Asn His Val Ser Ala Ile Asn Val Lys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: fragment

<400> SEQUENCE: 16

Val Thr Ala Gln Glu Leu Asp Tyr Leu Thr Arg
1               5                   10
```

```
<210> SEQ ID NO 17
<211> LENGTH: 12
<212> TYPE: PRT
<213> ORGANISM: Artificial Sequence
<220> FEATURE:
<223> OTHER INFORMATION: fragment

<400> SEQUENCE: 17

Asn Asn Thr Ser Phe Trp Phe Asp Leu Phe Pro Lys
1               5                   10

<210> SEQ ID NO 18
<211> LENGTH: 19
<212> TYPE: PRT
<213> ORGANISM: Artificial Sequence
<220> FEATURE:
<223> OTHER INFORMATION: fragment

<400> SEQUENCE: 18

Ser Phe Ser Tyr Asp Leu Phe Tyr Thr Gly Asp Gly Leu Pro Val Ser
1               5                   10                  15

Phe Leu Lys

<210> SEQ ID NO 19
<211> LENGTH: 15
<212> TYPE: PRT
<213> ORGANISM: Artificial Sequence
<220> FEATURE:
<223> OTHER INFORMATION: fragment

<400> SEQUENCE: 19

Tyr Ile Tyr Gly Gly Val Thr Leu Ala Gly Asp Tyr Leu Glu Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: fragment

<400> SEQUENCE: 20

Gly Ser Val Gly Ala Glu Phe Phe Gln Phe Tyr Ser Asp Asn Arg
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: fragment

<400> SEQUENCE: 21

Thr Val Asp Ile Tyr Gly Val Tyr Tyr Lys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: fragment

<400> SEQUENCE: 22

Val Ile Cys Ser Ala Glu Gly Ser Lys
1               5
```

```
<210> SEQ ID NO 23
<211> LENGTH: 11
<212> TYPE: PRT
<213> ORGANISM: Artificial Sequence
<220> FEATURE:
<223> OTHER INFORMATION: fragment

<400> SEQUENCE: 23

Pro Gly Gly Gly Ser His His His His His His
1               5                   10

<210> SEQ ID NO 24
<211> LENGTH: 204
<212> TYPE: PRT
<213> ORGANISM: Artificial Sequence
<220> FEATURE:
<223> OTHER INFORMATION: QCAT amino acid sequence

<400> SEQUENCE: 24

Met Gly Ala Lys Val Ile Arg Asn Val Thr Val Gln Glu Leu Asp Leu
1               5                   10                  15

Gln Ala Arg Gln Asn Thr Val Pro Leu Glu Thr Val Lys Tyr Asn Leu
            20                  25                  30

Tyr Asn Ser Asp Val Phe Asp Gly Lys Leu Gly Asn Tyr Asp Asn Val
        35                  40                  45

Arg Val Leu Asp Asp Asn His Val Ser Ala Ile Asn Val Lys Val Thr
    50                  55                  60

Ala Gln Glu Leu Asp Tyr Leu Thr Arg Tyr His Gln Leu Thr Gln Ile
65                  70                  75                  80

His Gly Leu Tyr Arg Leu Pro Thr Pro Ile Glu Leu Pro Leu Lys Asn
                85                  90                  95

Thr Asp Gly Ser Ile Ser Leu Ile Ile Phe Pro Ser Pro Tyr Tyr Ser
            100                 105                 110

Pro Ala Phe Thr Lys Asn Asn Thr Ser Phe Trp Phe Asp Leu Phe Pro
        115                 120                 125

Lys Ser Phe Ser Tyr Asp Leu Phe Tyr Thr Gly Asp Gly Leu Pro Val
    130                 135                 140

Ser Phe Leu Lys Tyr Ile Tyr Gly Gly Val Thr Leu Ala Gly Asp Tyr
145                 150                 155                 160

Leu Glu Lys Gly Ser Val Gly Ala Glu Phe Phe Gln Phe Tyr Ser Asp
                165                 170                 175

Asn Arg Thr Val Asp Ile Tyr Gly Val Tyr Tyr Lys Ala Gly Lys Val
            180                 185                 190

Ile Cys Ser Ala Glu Gly Ser Lys Ile Glu Gly Arg
        195                 200

<210> SEQ ID NO 25
<211> LENGTH: 636
<212> TYPE: DNA
<213> ORGANISM: Artificial Sequence
<220> FEATURE:
<223> OTHER INFORMATION: DNA sequence encoding QCAT amino acid sequence

<400> SEQUENCE: 25
attcaaccat gggtgcgaaa gttatccgta acgttaccgt gcaggaactg gacctgcagg      60
cgcgtcagaa cactgttccg ctggaaaccg taaaatacaa cctgtacaat tctgatgttt     120
tcgacggtaa actgggcaac tatgataacg tgcgtgtact gtatgatgac aaccacgtct     180
ccgctatcaa cgttaaagtg accgcacagg aactggacta cctgactcgc accaactga     240
```

| | | | | |
|---|---|---|---|---|
| cccagatcca | cggtctgtac | cgtctgccga | ccccgattga | gctgccactg aaaaacactg 300 |
| atggcagcat | ctctctgatc | attttcccgt | ccccgtacta | cagcccggcg tttactaaaa 360 |
| acaacaccag | cttctggttc | gacctgttcc | cgaaatcttt | ctcctatgac ctgttttaca 420 |
| ccggcgatgg | tctgccggtt | tcttttctga | aatacatcta | tggtggtgtg actctggcgg 480 |
| gcgattacct | ggagaagggt | tctgtgggcg | ccgaattctt | ccagttttat agcgacaatc 540 |
| gcaccgttga | catttacggc | gtgtactaca | aagctggcaa | agtaatttgc tctgcggaag 600 |
| gttccaaaat | cgaaggtcgt | cccgggtata | ttgtca | 636 |